United States Patent
Lal et al.

(10) Patent No.: US 6,322,977 B1
(45) Date of Patent: Nov. 27, 2001

(54) TAPASIN-LIKE PROTEIN

(75) Inventors: Preeti Lal, Santa Clara; Matthew R. Kaser, Castro Valley; Mariah R. Baughn, San Leandro, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/292,097

(22) Filed: Apr. 14, 1999

(51) Int. Cl.[7] .............................. C12Q 1/68; C07K 14/00; C07H 21/04
(52) U.S. Cl. ........................ 435/6; 435/69.1; 536/23.1; 536/24.3; 530/350; 530/324; 530/325
(58) Field of Search ................................. 536/23.1, 24.3; 435/6, 69.1; 530/350, 324, 325

(56) References Cited

FOREIGN PATENT DOCUMENTS

WO 99/52928 * 10/1999 (WO).

OTHER PUBLICATIONS

Pamer, E., et al., Abstract, Mechanisms of MHC class I—restricted antigen processing, *Ann Rev Immunol*, 16:323–58, (1998).
Ortmann, B., et al., Abstract, A critical role for tapasin in the assembly and function of multimeric MHC class I–TAP complexes, *Science*, 277 (5330):1306–9, (1997).
Lewis, JW, et al., Abstract, HLA–A *0201 presents TAPdependent peptide epitopes to cytotoxic T lymphocytes in the absence of tapasin, *Eur J Immunol*, 28(10):3214–20, (1998).
Suh, WK, et al., Abstract, Interaction of murine MHC class I molecules with tapasin and TAP enhances peptide loading and involves the heavy chain alpha3 domain, *J Immunol*, 162(3):1530–40, (1999).
Lewis, JW, et al., Abstract, Evidence for successive peptide binding and quality control stages during MHC class I assembly, *Curr Biol*, 8(12):717–20, (1998).
Grandea, A.G., et al., (Direct Submission), GenBank Sequence Database (Accession AFO43943), National Center for Biotechnology Information, National Library of Medicine, Bethesda, Maryland, 20894 (GI 3169278).
Frangoulis, B., et al., (Direct Submission), GenBank Sequence Database (Accession 3183699), National Canter for Biotechnology Information, National Library of Medicine, Bethesda, Maryland, 20894 (GI 3183699).
Elferink, L.A., et al., (Direct Submission), GenBank Sequence Database (Accession M24104 J04827), National Center for Biotechnology Information, National Library of Medicine, Bethesda, Maryland, 20894 (GI 207628).
Ravichandran, V., et al., Identification of a Novel Syntaxin—and Synaptobrevin/VAMP–binding Protein, SNAP–23, Epxressed in Non–neuronal Tissues, *The Journal of Biological Chemistry*, 271(23):13300–13303, (1996).
Herberg et al., Eur. J. Immunol. 28(2), 459–467, 1998.*
Granden et al, Immungenetics, 48(4), 260–265, 1998.*

* cited by examiner

*Primary Examiner*—Bennett Celsa
(74) *Attorney, Agent, or Firm*—Incyte Genomics, Inc.; Lynn E. Murry

(57) ABSTRACT

The invention provides a mammalian nucleic acid sequence and fragments thereof. It also provides for the use of the nucleic acid sequence for the characterization, diagnosis, evaluation, treatment, or prevention of conditions, diseases and disorders associated with gene expression and for the production of a model system. The invention additionally provides expression vectors and host cells for the production of the protein encoded by the mammalian nucleic acid sequence.

8 Claims, 13 Drawing Sheets

FIGURE 1A

Figure 2A:
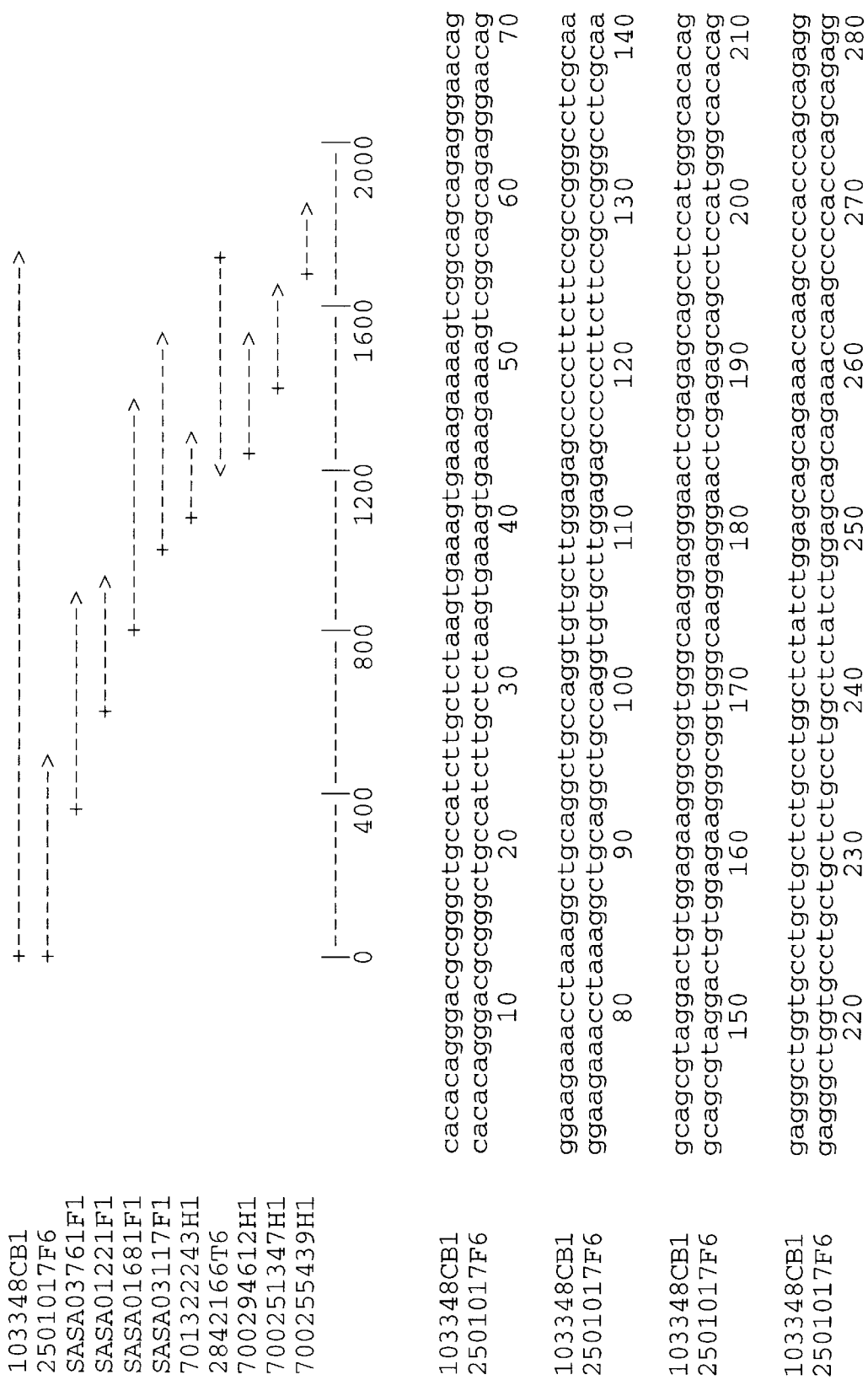

```
                    9          18          27          36          45          54
5' CAC ACA GGG    ACG CGG GCC    ATC TTG CTC    TAA GTG AAA    GAA AAG TCG 63          72          81          90          99         108
   GCA GCA GAG    GGA ACA GGG    AAG AAA CCT    AAA GGC TGC    AGG CTG CCA    GGT GTG CTT 117         126         135         144         153         162
   GGA GAG CCC    CCT TCT TCC    GCC GGG CCT    CGC AAG CAG    CGT AGG CTG    GAG AAG 171         180         189         198         207         216
   GGC GGT GGG    CAA GGA AAC    TCG AGA GCA    TCC ATG GGC    ACA CAG GAG    GGC
                                                      M   G     T   Q   E     G 225         234         243         252         261         270
   TGG TGC CTG    CTG CTC TGC    CTA TCT GGA    GCA GCA GAA    ACC AAG CCC    CAC
   W   C   L      L   L   C      L   S   G      A   A   E      T   K   P      H 279         288         297         306         315         324
   CCA GCA GAG    GGG CAG CGG    GCA GGA GCT    CGG CAG GTG    GAC GTG CTC    GAC AGC TGC    TTC CTG GCG
   P   A   E      G   Q   R      A   G   A      L   A   V      D   V   L      D   S   C      F   L   A 333         342         351         360         369         378
   AAG GAC GGT    GCG CAC CGT    GGA GCT CTC    CGG CAG GTC    GTC AGT GAG    GAC AGG GCA    AGG GCA GCC
   K   D   G      A   H   R      G   A   L      R   Q   V      V   S   E      D   R   A      R   A   A 387         396         405         414         423         432
   TCC CTT GTG    CTG AAG CAG    GTG CCA CTG    GAC GAT GGC    TCC CTG GAG    GAC TTC
   S   L   V      L   K   Q      V   P   L      D   D   G      S   L   E      D   F
```

FIGURE 1B

```
441                 450                 459                 468                 477             486
ACC GAT TTC CAA    GGG GGC ACA CTG    GCC CAA GAT CCA    CCT ATT ATC TTT    GAG
 T   D   F   Q      G   G   T   L      A   Q   D   P      P   I   I   F      E 495                 504                 513                 522                 531             540
GCC TCA GTG GAC    CTG GTC CAG ATT    CCC CAG GCC TTG    CTC CAT GCT GAC
 A   S   V   D      L   V   Q   I      P   Q   A   L      L   H   A   D 549                 558                 567                 576                 585             594
TGC AGT GGG AAG    GAG GTG ACC TGT    GAG ATC TCC CGC    TAC TTT CAG ATG    ACA
 C   S   G   K      E   V   T   C      E   I   S   R      Y   F   Q   M      T 603                 612                 621                 630                 639             648
GAG ACC GTT AAG    ACA GCA GCT TGG    TTC ATG GCC AAC    ATG CAG GTC TCT    GGA
 E   T   V   K      T   A   A   W      F   M   A   N      M   Q   V   S      G 657                 666                 675                 684                 693             702
GGG GGA CCT AGC    ATC TCC TTG GTG    ATG AAG ACT CCC    AGG GTC ACC AAG    AAT GAG
 G   G   P   S      I   S   L   V      M   K   T   P      R   V   T   K      N   E 711                 720                 729                 738                 747             756
GCG CTC TGG CAC    CCG ACG CTG AAC    TTG CCA AGC CCC    CAG GGG ACT GTG    CGA
 A   L   W   H      P   T   L   N      L   P   S   P      Q   G   T   V      R 765                 774                 783                 792                 801             810
ACT GCA GTG GAG    TTC CAG GTG ATG    ACA CAG ACC CAA    TCC CTG AGC TTC    CTG
 T   A   V   E      F   Q   V   M      T   Q   T   Q      S   L   S   F      L
```

```
        819           828           837       846           855       864
GGG TCC TCA GCC TCC TTG GAC TGT GGC TTC TCC ATG GCA CCG GGC TTG GAC CTC
 G   S   S   A   S   L   D   C   G   F   S   M   A   P   G   L   D   L 873           882           891       900           909       918
ATC AGT GTG GAG TGG CGA CTG CAG CAC AAG GGC AGG GGT CAG TTG GTG TAC AGC
 I   S   V   E   W   R   L   Q   H   K   G   R   G   Q   L   V   Y   S 927           936           945       954           963       972
TGG ACC GCA GGG CAG GGG CAG GCT GTG CGG AAG GGC GCT ACC CTG GAG CCT GCA
 W   T   A   G   Q   G   Q   A   V   R   K   G   A   T   L   E   P   A 981           990           999       1008          1017      1026
CAA CTG GGC ATG GCC AGG GAT GCC CTC ACC CTG CCC GGC CTC ACT ATA CAG
 Q   L   G   M   A   R   D   A   L   T   L   P   G   L   T   I   Q 1035          1044          1053      1062          1071      1080
GAC GAG GGG ACC TAC ATT TGC CAG ATC ACC ACC TCT CTG TAC CGA GCT CAG CAG
 D   E   G   T   Y   I   C   Q   I   T   T   S   L   Y   R   A   Q   Q 1089          1098          1107      1116          1125      1134
ATC ATC CAG CTC AAC ATC CAA GCT TCC CCT AAA GTA CGA CTG AGC TTG GCA AAC
 I   I   Q   L   N   I   Q   A   S   P   K   V   R   L   S   L   A   N 1143          1152          1161      1170          1179      1188
GAA GCT CTG CTG CCC ACC CTC ATC TGC GAC ATT GCT GGC TAT TAC CCT CTG GAT
 E   A   L   L   P   T   L   I   C   D   I   A   G   Y   Y   P   L   D
```

FIGURE 1C

|  | 1197 | 1206 | 1215 | 1224 | 1233 | 1242 |
|---|---|---|---|---|---|---|
| GTG | GTG | ACG | TGG | ACC | CGA | GAG | CTG | GGT | GGA | TCC | CCA | GCC | CAA | GTC | TCT |
| V | V | T | W | T | R | E | E | L | G | G | S | P | A | Q | V | S |

|  | 1251 | 1260 | 1269 | 1278 | 1287 | 1296 |
|---|---|---|---|---|---|---|
| GGT | GCC | TCC | TTC | TCC | AGC | CTC | AGG | CAA | AGC | GTG | GCA | GGC | TAC | AGC | ATC | TCC |
| G | A | S | F | S | S | L | R | Q | S | V | A | G | Y | S | I | S |

|  | 1305 | 1314 | 1323 | 1332 | 1341 | 1350 |
|---|---|---|---|---|---|---|
| TCC | TCT | CTC | ACC | GCA | GAA | CCT | GGC | TCT | GCA | GGT | GCC | ACT | TAC | ACC | TGC | CAG | GTC |
| S | S | L | T | A | E | P | G | S | A | G | A | T | Y | T | C | Q | V |

|  | 1359 | 1368 | 1377 | 1386 | 1395 | 1404 |
|---|---|---|---|---|---|---|
| ACA | CAC | ATC | TCT | CTG | GAG | GAG | CCC | CTT | GGG | GCC | AGC | ACC | CAG | GTT | GTC | CCA | CCA |
| T | H | I | S | L | E | E | P | L | G | A | S | T | Q | V | V | P | P |

|  | 1413 | 1422 | 1431 | 1440 | 1449 | 1458 |
|---|---|---|---|---|---|---|
| GAG | CGG | AGA | ACA | GCC | TTG | GGA | GTC | ATC | TTT | GCC | CAA | GCA | AGT | CTC | TTC | CTT | GCA |
| E | R | R | T | A | L | G | V | I | F | A | Q | A | S | L | F | L | A |

|  | 1467 | 1476 | 1485 | 1494 | 1503 | 1512 |
|---|---|---|---|---|---|---|
| CTG | ATG | TTC | CTG | GGG | CTT | CAG | AGA | CGG | CAA | GCA | CCT | ACA | GGA | CTT | GGG | CTG | CTT |
| L | M | F | L | G | L | Q | R | R | Q | A | P | T | G | L | G | L | L |

|  | 1521 | 1530 | 1539 | 1548 | 1557 | 1566 |
|---|---|---|---|---|---|---|
| CAG | GCT | GAA | CGC | TGG | GAG | ACC | ACT | TCC | TGT | GCT | GAC | ACA | CAG | TCC | AGC | CAT | CTC |
| Q | A | E | R | W | E | T | T | S | C | A | D | T | Q | S | S | H | L |

FIGURE 1D

```
         1575           1584           1593          1602          1611          1620
CAT GAA GAC CGC ACA GCG CGT GTA AGC CAG CCC AGC TGA CCT AAA GCG ACA TGA
 H   E   D   R   T   A   R   V   S   Q   P   S 1629           1638           1647          1656          1665          1674
GAC TAC TAG AAA GAA ACG ACA CCC TTC CCC AAG CCC CCA CAG CTA CTC CAA CCC 1683           1692           1701          1710          1719          1728
AAA CAA CCA AGC CAG TTT AAT GGT AGG AAT TTG TAT TTT TTG CCT TTG TTC 1737           1746           1755          1764
AGA ATA CAT GAC ATT GGT AAA TAT GCC ACA TGC CTT 3'
```

FIGURE 1E

```
103348CB1      ggcagtggcgggcagtggacgtggtcctagactgctccctggcgaaggacggtgcgcaccgtggagctct
2501017F6      ggcagtggcgggcagtggacgtggtcctagactgctccctggcgaaggacggtgcgcaccgtggagctct
                      290              300              310              320              330              340              350

103348CB1      cgccagcagtg*aggacagggcaagggcctcccttgtgctgcagtgtgccagtgctgacgatggctc
2501017F6      cgccagcagtgtaggacagggcaagggcctcccttgtgctgcagtgtgccagtgctgacgatggctc
SASA03761F1    ...................................................tcccntggaagnaantt
                      360              370              380              390              400              410              420

103348CB1      cctggaggacttcaccgatttccaaggggcacactgg*cccaagatgacccacct*attatctttgagg
2501017F6      cctggaggacttcaccgatttccaaggggcacactggncacactggncccaactnattaactttgagg
SASA03761F1    caccggatttccaaagggggncaaaantggcccnaan*gattgaccaacntaat*naacttttgaagc
                      430              440              450              460              470              480              490

103348CB1      cctca*gtggacct*ggtccaga*ttccccaggcc*gaggccttgctcc*atgctgactgcagtgggaag
2501017F6      gctcaagtggacct*ggtccaaaattcccaggcc*gaggcttt......................
SASA03761F1    cntcaagtggacttggtccaagatccccaagccccgagccctgctcccatgcctgctnactgcagtggaaag
                      500              510              520              530              540              550              560

103348CB1      gaggtgacctgtgagatctcccgctactttctccagatgacagagaccactgttaagacagcagcttggt
SASA03761F1    gagttgacctgtgagatctcccgctactttctccagatgacagagaccactgttaagacagcagcttggt
                      570              580              590              600              610              620              630

103348CB1      tcatggccaacatgCAGGTCTCTTGGAGGGGACCTAGCATCTCCTTGGTGATGAAGACTCCCAGGGTCAC
SASA03761F1    tcatggccaacatgCAGGTCTCTTGGAGGGGACCTAGCATCTCCTTGGTGATGAAGACTCCCAGGGTCAC
SASA01221F1    ......cccaacatgCAGGTCTCTTGGAGGGGACCTAGCATCTCCTTGGTGATGAAGACTCCCAGGGTCAC
                      640              650              660              670              680              690              700

103348CB1      CAAGAATGAGGcgctctggcacCCGACGCTGAACTTGCCACTGAGCCCCCAGGGGACTGTGCGAACTGCA
SASA03761F1    CAAGAATGAGGcgctctggcacCCGACGCTGAACTTGCCACTGAGCCCCCAGGGGACTGTGCGAACTGCA
SASA01221F1    CAAGAATGAGGcgctctngcacCCGACGCTGAACTTGCCACTGAGCCCCCAGGGGACTGTGCGAACTGCA
                      710              720              730              740              750              760              770
```

FIGURE 2B

```
103348CB1       GTGGAGTTCCAGGTGATGATGACACAGACCCAATCCCTGAGCTTCCTGCTGGGTCCTCAGCCTCCTTGACT
SASA03761F1     GTGGAGTTCCAGGTGATGATGACACAGACCCAATCCCTGAGCTTCCTGCTGGGTCCTCAGCCTCCTTGACT
SASA01221F1     GTGGAGTTCCAGGTGATGATGACACAGACCCAATCCCTGAGCTTCCTGCTGGGTCCTCAGCCTCCTTGACT
SASA01681F1     ........................................................cggggnttttn
                        780       790       800       810       820       830       840

103348CB1       GTGGCTTCTCCATGGCACCGGCTTGACCTCATCAGTGTGGAGTGGCGACTGCAGCACAAGGGCAGGg
SASA03761F1     GTGGCTTCTCCATGGCACCGGCTTGACCTCATCAGTGTGGAGTGGCGACTGCAGCACAAGGGCAGGg
SASA01221F1     GTGGCTTCTCCATGGCACCGGCTTGACCTCATCAGTGTGGAGTGGCGACTGCAGCACAAGGGCAGGg
SASA01681F1     gaacccttcnaatcaattgttgggaanttngcnaantggccaagcaacaaggngcaagggttcaagtt
                        850       860       870       880       890       900       910

103348CB1       tcagttggtgtacAGCTGGACCGCAGGG**CAGGGGCAGGCTGTGCGGAAGGGC*GCTACCctggagcc*
SASA03761F1     tcagttggtgtacAGCTGGACCGCAGGG**CAGGGGCAGGCTGTGCGGAAGGGC*GCTACCctggagngg
SASA01221F1     tcngttggtgtacAGCTGGACCGCAGGG**CAGGGGCAGGCTGTGCGGAAGGGC*GCTACCctggagcc*
SASA01681F1     ngggtgtaacaagcttggaaccgcaggngcagnctntgcggaaaggccgctaccttggagccc
                        920       930       940       950       960       970       980

103348CB1       tgcACAACTGGGCATGGCCAGggatgcctccctcacCctgcccggcctcacTATACAGGACGAGGGACC
SASA03761F1     nntccctctagagtcgacctgc.............................................
SASA01221F1     tgcACAACTGGGCATGGCCAGggatgcctcccctgcctccctccacccctgcccgg............
SASA01681F1     tgcACAACTGGGCATGGCCAGggatnccctccttcacccgccgcctcacTATACAGGACGAGGGACC
                ..........caggtcgactctagaggntcccccctcacTATACAGGACGAGGGACC
                        990      1000      1010      1020      1030      1040      1050

103348CB1       TACATTTGCCAGATCACCACCTCTCTGTACCGAGCTCAGCAGATCAT*CCAGCTCAACATCCAAGCTTCC
SASA03761F1     TACATTTGCCAGATCACCACCTCTCTGTACCGAGCTCAGCAGATCAT*CCAGCTCAACATCCAAGCTTCC
SASA01221F1     TACATTTGCCAGATCACCACCTCTCTGTACCGAGCTCAGCAGATCAT*CCAGCTCAACATCCAAGCTTCC
SASA01681F1     TACATTTGCCAGATCACCACCTCTCTGTACCGAGCTCAGCAGATCAT*CCAGCTCAACATCCAAGCTTCC
7013122243H1    ........aagctcaacagatcatgcca*cttaacatcctggctccc
                        1060      1070      1080      1090      1100      1110      1120
```

FIGURE 2C

```
103348CB1       CCTAAAGTACGACTGAGCTTGGCAAACGAAGCTCTGCTGCTGCCCACCCTCATCTGCGACATTGCTGGCTATT
SASA01681F1     CCTAAAGTACGACTGAGCTTGGCAAACGAAGCTCTGCTGCTGCCCACCCTCATCTGCGACATTGCTGGCTATT
SASA03117F1     CCTAAAGTACGACTGAGCTTGGCAAACGAAGCTCTGCTGCTGCCCACCCTCATCTGCGACATTGCTGGCTATT
7013222243H1    cccaaagtacaactgcactggcaaacaaggatccctcctgcgtctgcagcattgccggctact
2842166T6
700294612H1
                                              1130      1140      1150      1160      1170      1180      1190

103348CB1       ACCCTCTGGATGTGGTGGTGGTGTGGGTGACGTGGACGTGGACCCCGAGAGAGAGCTGGGTGATCCCCAGCCCCAAGTCTCTGGTGC
SASA01681F1     ACCCTCTGGATGTGGTGGTGGTGTGGGTGACGTGGACGTGGACCCCGAGAGAGAGCTGGGTGATCCCCAGCCCCAAGTCTCTGGTGC
SASA03117F1     ACCCTCTGGATGTGGTGGTGGTGTGGGTGACGTGGACGTGGACCCCGAGAGAGAGCTGGGTGATCCCCAGCCCCAAGTCTCTGGTGC
7013222243H1    atcctctggatgtgtgggagtgacgtgattcgagAGGAGCTGGtggaattccagcCCAAGTCTCTGGtgc
2842166T6                                                                                .tatgttcctggggcttcagagacg
700294612H1                                                                                           .tctctggngc
                                              1200      1210      1220      1230      1240      1250      1260

103348CB1       CTCCTTCTCCAGCCTCAGGCAAAGCCGTGGCAGGCACCTACAGCATCTCCTCCTCCTCCTCCTCCTCCACCGCagaa*cc
SASA01681F1     CTCCTTCTCCAGCCTCAGGCAAAGCCGTGGCAGGCACCTACAGCATCTCCTCCTCCTCCTCCTCCTCCACCGCagaa*cc
SASA03117F1     CTCCTTCTCCAGCCTCAGGCAAAGCCGTGGCAGGCACCTACAGCATCTCCTCCTCCTCCTCCTCCTCCACCGCagaa*cc
7013222243H1    ctc*ttctccagcntcaggcagagacgatggtaacttacagcnttgttcangtgaggctgacca*gc
2842166T6       gcaagagtagaacaagagtagtcacgtgctcccccagaagaacttacagcatttaagtcaagtcacagagg*tt
700294612H1     ctcctttctccaancctcagacagaacatgatgggaacctacagcattcttccacggtgannccganncc
                                              1270      1280      1290      1300      1310      1320      1330

103348CB1       tggctcTGCAGGTGCCACTTACACCTGCCAGGTCACACACATCTCTCTGGAGGAGCCCCTTGGGGCCAGC
SASA01681F1     tggctcTGCAGGTGCCACTTACACCTGCCAGGTCACACACATCTCTCTGGAGGAGCCCCTTGGGGCCAGC
SASA03117F1     cggctcTGCCAGGTGCCACTTACACCTGCCAGGTCACACACATCTCTCTGGAGGAGCCCCTTGGGGCCAGC
7013222243H1    c.......................................
2842166T6       aaaaatacatgaaggtggcaccagtcatgggcactggcctgctctgcagaggcctctgcctcctt
700294612H1     angccncacaggtgcnacttacacctgccaagtcgccacgtctccctganagagagcccctganagtcagc
                                              1340      1350      1360      1370      1380      1390      1400
```

FIGURE 2D

```
103348CB1       ACCCAGGTTGTCCCA**C*CAGAGCGGAGAacagcccttgggagtcatctttgccagcagtctcttcctc
SASA01681F1     ACCCAGGTTGTCCCA**C*CAGAGCGGAGAacagcccttgggagtcatctttgccagcagtctcttcctc
SASA03117F1     ACCCAGGTTGTCCCA**C*CAGAGCGGAGAacagcccttgggagtcatctttgccagcagtctcttcctc
2842166T6                                  cactgtgcaccctgg**g*ctcatgcaccaaggcagagaacagagaagtgaggggacaagaagagc
7002946I2H1                                atganggttttgccaaacacacagagcanagaggagccttgggagtcatcgttgccancatcctctncttt
7002513471H1                               ...gttttgccaaac**a*cagagcaaagaggagccttgggagtcatcgttgccagcatcctcttccttt
                                           1410      1420      1430      1440      1450       1460      1470

103348CB1       ttgcactgatgttcctggggc**ttcagagacgg*cctacagg*actt**gggct*gctt*ca
SASA03117F1     ttgcactgatgtncctggggggtttcagagacgggcnagcaacctatagggactttggggcttgctttca
2842166T6       agaatgtccagatggaggataagaccaaagagccagca*cctacagg*actt**gggct*gctt*aa
7002946I2H1     ttgngctcttgctcctgggac***ttcntngacag*naagct*tcatcatc*anag**ttcnn*caag*tc
7002513471H1    ttgcgctcttgctcctgggac**ttcatagacag*caagct*tcancatc*aaag*tccac*caag*tc
                         1480      1490      1500      1510      1520      1530      1540

103348CB1       ggctgaa*cgct*ggga*gacc*acttcctgtgctgacacacagagctccatctccatgaagaccgcac
SASA03117F1     ggctgaaacgcttgggaagaagaccactnncctggccngananananaana.........
2842166T6       ggctgaa*cgct*ggga*gacc*acttcctgtgctgacacacagagctccatctccatgaagaccgcac
7002946I2H1     tgtgagg*nact*ctga*gtag*ncgctttnctgccc.........
7002513471H1    tgtgagg*cact*ctga*gtag*ccgcttccctgcctccgagtacaaagaaaagctctcgtgttctagct
                         1550      1560      1570      1580      1590      1600      1610

103348CB1       agcgcgtgtaagccagcccagctgacctaaagcgacatgagactactagaaagaacgacaccctcccc
2842166T6       agcgcgtgtaagccagcccagctgacctaaagcgacatgagactactagaaagaacgacaccctcccc
7002513471H1    acctaagaaccctgtgttgaggtgtgggactgagacgggcctgaaggaggcagcacattgggagtgaggt
                         1620      1630      1640      1650      1660      1670      1680
```

FIGURE 2E

```
103348CB1    aagccccacagctactccaacccaaacaacaaccaagccagtttaatggtaggaatttgtatttttgc
2842166T6    aagcccnacagctactccaacccaaacaacaaccaagccagtttaatggtaggaatttgtatttttgc
7002946I2H1  ....................................................................
7002513471H1 ....................................................................
7002554391H1 ........................................................tttgtggtaggaatttgtatttttgc
                   1690      1700      1710      1720      1730      1740      1750

103348CB1    ctttgttcagaatacatgacattggtaaatatgccacatgcctt........................
2842166T6    ctttgttcagaatacatgacattggtaaatatgccacatgcctt........................
7002554391H1 ctttgttgagaatacatgagattggtaaatctgtcacatgcctttggtggaaggacnactcttactacta
                   1760      1770      1780      1790      1800      1810      1820

7002554391H1 tacataaactgtgagactgggttaggaaagacacggtggtaatgacagacacaatggaaaccccacatca
                   1830      1840      1850      1860      1870      1880      1890

7002554391H1 cctcatggcaaacaaagaggatgtgggaagcttggcttcaactga........................
                   1900      1910      1920      1930      1940      1950      1960
```

FIGURE 2F

```
1   MGTQEGWCLLLCLALSGAAAETKPHPAEGQWRAVDVVLDCF          103348
1   MKPLL----LLVAVALGLATFVSVVSAGPE-----AIECW          g3169279
1   MAAGL----RLL-----------------LAGGGAR----G         g3183699

41  LAKDGAHRGALASSEDRARASLVLKQVPVLDDGSLEDFTD           103348
32  FVEDAG----GGGLSKKPATLLLRHGPRGPPPR-------           g3169279
17  ---RAA----GGGQCPSCTAALW---GGRGDPSR-----            g3183699

81  FQGGTLAQDDPPIIFEASVDLVQIPQAEALLHADCSGKEV           103348
61  ----PDLDPKLYFKVDDPAGMLLAAFRRYPAGASAPH---           g3169279
41  TRPGARSHLQCQRPLGD--SSPTRVPP-RTPPS------           g3183699

121 TCEISRYFLQMTETTVKTAAWFMANMQVSGGGPSIS----           103348
94  -CEMSRF-----IPFPASAKWARSLSPEQNCPRALDGDWL           g3169279
71  -CELNPT---NPQTGSDPWSRPLHPDARSPPTAGGQWW             g3183699

157 LVMKTPRVTKNEALWHPTLNLPLSPQGTV-RTAVEFQVMT           103348
128 LVSVSSTLFSLSLLRPQPE-PLREPVVITMATVVLTVLT           g3169279
105 VAAVGTPQYGVTALLQ---G-GMGTEGTHT-AAVALAVLT           g3183699

196 QTQSLSFLLGSSASLD--CGFSMA----PGLDL------           103348
167 HNPAPRVQLGKDAVLDLRFAYAPSALEGSPSLDAGPPPFG           g3169279
140 HTPTLRARVG--SPIHLHCAFAAP-----PSSFV-----           g3183699

225 VEWRLQHKGRGQLVYSWTAGQGQAVRKGATLEPAQLGMAR           103348
207 LEWRRQHRGKGHLLL--AATPGLAGRMPPAQEKATAFAAW           g3169279
167 LEWRHQNRGAGRVLL--AYDSS-TARAPRAHPGAELLLGT           g3183699
```

FIGURE 3A

```
265  D- - - - - - - - - ASLTLPGLTIQDEGTYICQITTSLYRAQ      103348
245  DDDEPWGPWTGNGTFWLPAVKPSQEGVYLGTVHLPYLQGQ              g3169279
204  RDGDG- - - VTAVTLRLARPSPGDEGTYICSVFLPHGHTQ            g3183699

294  QIIQLNIQASPKVRLS- - - - -LANEALLPTLICDIAGYY           103348
285  VSLELTVHKGPRVSLTPAPVVWAAPGEAPPELLCLASHFF              g3169279
240  TVLQLHVFEPPKVTLSPKNLV-VAPG-TSAELRCHVSGFY              g3183699

328  PLDVV- VTWTREELGGSPAQ- - - -VSGASFSSLRQSVAG          103348
325  PAEGLEVKWELRGGPGGSS- - -RKVEGKTWLSTIRHHSDG           g3169279
278  PLD-VTVTWQRRAGGSGTSQSPRDTVMDSWTSGHRQAADG              g3183699

362  TYSISSSLTAEPGSA- - -GATYTCQVTHISLEEPLGASTQ            103348
362  SVSQSGHLQLPPVTAKQHGVHYVCRVYHSSLPASGRSADV              g3169279
317  TYSRTAAARLIPARPQHHGDIYSCVVTHTALAKPMR-VSV              g3183699

399  VVPPERRTALGVIFASSLFLLALMFLGLQRRQAPTGLGLL              103348
402  TLEVAGFSGPSIEDGIGLFLSAFLLLGLLK- - - -VLGWL            g3169279
356  RLLAGTEGPHLEDITGLFLVAFVLCGLIR- - - - -                g3183699

439  QAERWETTSCADTQSSHLHEDRTARVSQPS                        103348
437  AAY-WTIPEVSKEKATAASLTIPRNSKKSQ                        g3169279
386  - - -WLYPKAARPKE- - - - -ETKKSQ                      g3183699
```

FIGURE 3B

SEQUENCE LISTING

```
<160> NUMBER OF SEQ ID NOS: 17

<210> SEQ ID NO 1
<211> LENGTH: 1764
<212> TYPE: DNA
<213> ORGANISM: Homo sapiens
<220> FEATURE: -
<223> OTHER INFORMATION: 103348CB1

<400> SEQUENCE: 1
cacacaggga cgcgggctgc catcttgctc taagtgaaag tgaaagaaaa gtcggcagca      60
```

-continued

```
gagggaacag ggaagaaacc taaaggctgc aggctgccag gtgtgcttgg agagccccct      120
tcttccgccg ggcctcgcaa gcagcgtagg actgtggaga agggcggtgg gcaaggaggg      180
aactcgagag cagcctccat gggcacacag gagggctggt gcctgctgct ctgcctggct      240
ctatctggag cagcagaaac caagccccac ccagcagagg ggcagtggcg ggcagtggac      300
gtggtcctag actgcttcct ggcgaaggac ggtgcgcacc gtggagctct cgccagcagt      360
gaggacaggg caagggcctc ccttgtgctg aagcaggtgc cagtgctgga cgatggctcc      420
ctggaggact tcaccgattt ccaagggggc acactggccc aagatgaccc acctattatc      480
tttgaggcct cagtggacct ggtccagatt ccccaggccg aggccttgct ccatgctgac      540
tgcagtggga aggaggtgac ctgtgagatc tcccgctact ttctccagat gacagagacc      600
actgttaaga cagcagcttg gttcatggcc aacatgcagg tctctggagg gggacctagc      660
atctccttgg tgatgaagac tcccaggggtc accaagaatg aggcgctctg cacccgacg      720 ctgaacttgc cactgagccc ccaggggact gtgcgaactg cagtggagtt ccaggtgatg      780
acacagaccc aatccctgag cttcctgctg gggtcctcag cctccttgga ctgtggcttc      840
tccatggcac cgggcttgga cctcatcagt gtggagtggc gactgcagca aagggcagg      900 ggtcagttgg tgtacagctg gaccgcaggg caggggcagg ctgtgcggaa gggcgctacc      960
ctggagcctg cacaactggg catggccagg gatgcctccc tcaccctgcc cggcctcact      1020
atacaggacg aggggaccta catttgccag atcaccacct ctctgtaccg agctcagcag      1080
atcatccagc tcaacatcca agcttccccct aaagtacgac tgagcttggc aaacgaagct      1140
ctgctgccca ccctcatctg cgacattgct ggctattacc ctctggatgt ggtggtgacg      1200
tggacccgag aggagctggg tggatcccca gcccaagtct ctggtgcctc cttctccagc      1260
ctcaggcaaa gcgtggcagg cacctacagc atctcctcct ctctcaccgc gaacctggc      1320 tctgcaggtg ccacttacac ctgccaggtc acacacatct ctctggagga gccccttggg      1380
gccagcaccc aggttgtccc accagagcgg agaacagcct tgggagtcat ctttgccagc      1440
agtctcttcc ttcttgcact gatgttcctg gggcttcaga cacggcaagc acctacagga      1500
cttgggctgc ttcaggctga acgctgggag accacttcct gtgctgacac acagagctcc      1560
catctccatg aagaccgcac agcgcgtgta agccagccca gctgacctaa agcgacatga      1620
gactactaga aagaaacgac acccttcccc aagcccccac agctactcca acccaaacaa      1680
caaccaagcc agtttaatgg taggaatttg tattttttgc ctttgttcag aatacatgac      1740
attggtaaat atgccacatg cctt                                            1764
```

<210> SEQ ID NO 2
<211> LENGTH: 468
<212> TYPE: PRT
<213> ORGANISM: Homo sapiens
<220> FEATURE: -
<223> OTHER INFORMATION: 103348CD1

<400> SEQUENCE: 2

Met Gly Thr Gln Glu Gly Trp Cys Leu Leu Leu Cys Leu Ala Leu
 1               5                  10                  15

Ser Gly Ala Ala Glu Thr Lys Pro His Pro Ala Glu Gly Gln Trp
                20                  25                  30

Arg Ala Val Asp Val Val Leu Asp Cys Phe Leu Ala Lys Asp Gly
                35                  40                  45

Ala His Arg Gly Ala Leu Ala Ser Ser Glu Asp Arg Ala Arg Ala

-continued

```
                    50                  55                  60
Ser Leu Val Leu Lys Gln Val Pro Val Leu Asp Asp Gly Ser Leu
                65                  70                  75
Glu Asp Phe Thr Asp Phe Gln Gly Gly Thr Leu Ala Gln Asp Asp
                80                  85                  90
Pro Pro Ile Ile Phe Glu Ala Ser Val Asp Leu Val Gln Ile Pro
                95                 100                 105
Gln Ala Glu Ala Leu Leu His Ala Asp Cys Ser Gly Lys Glu Val
               110                 115                 120
Thr Cys Glu Ile Ser Arg Tyr Phe Leu Gln Met Thr Glu Thr Thr
               125                 130                 135
Val Lys Thr Ala Ala Trp Phe Met Ala Asn Met Gln Val Ser Gly
               140                 145                 150
Gly Gly Pro Ser Ile Ser Leu Val Met Lys Thr Pro Arg Val Thr
               155                 160                 165
Lys Asn Glu Ala Leu Trp His Pro Thr Leu Asn Leu Pro Leu Ser
               170                 175                 180
Pro Gln Gly Thr Val Arg Thr Ala Val Glu Phe Gln Val Met Thr
               185                 190                 195
Gln Thr Gln Ser Leu Ser Phe Leu Leu Gly Ser Ser Ala Ser Leu
               200                 205                 210
Asp Cys Gly Phe Ser Met Ala Pro Gly Leu Asp Leu Ile Ser Val
               215                 220                 225
Glu Trp Arg Leu Gln His Lys Gly Arg Gly Gln Leu Val Tyr Ser
               230                 235                 240
Trp Thr Ala Gly Gln Gly Gln Ala Val Arg Lys Gly Ala Thr Leu
               245                 250                 255
Glu Pro Ala Gln Leu Gly Met Ala Arg Asp Ala Ser Leu Thr Leu
               260                 265                 270
Pro Gly Leu Thr Ile Gln Asp Glu Gly Thr Tyr Ile Cys Gln Ile
               275                 280                 285
Thr Thr Ser Leu Tyr Arg Ala Gln Gln Ile Ile Gln Leu Asn Ile
               290                 295                 300
Gln Ala Ser Pro Lys Val Arg Leu Ser Leu Ala Asn Glu Ala Leu
               305                 310                 315
Leu Pro Thr Leu Ile Cys Asp Ile Ala Gly Tyr Tyr Pro Leu Asp
               320                 325                 330
Val Val Val Thr Trp Thr Arg Glu Glu Leu Gly Gly Ser Pro Ala
               335                 340                 345
Gln Val Ser Gly Ala Ser Phe Ser Ser Leu Arg Gln Ser Val Ala
               350                 355                 360
Gly Thr Tyr Ser Ile Ser Ser Ser Leu Thr Ala Glu Pro Gly Ser
               365                 370                 375
Ala Gly Ala Thr Tyr Thr Cys Gln Val Thr His Ile Ser Leu Glu
               380                 385                 390
Glu Pro Leu Gly Ala Ser Thr Gln Val Val Pro Pro Glu Arg Arg
               395                 400                 405
Thr Ala Leu Gly Val Ile Phe Ala Ser Ser Leu Phe Leu Leu Ala
               410                 415                 420
Leu Met Phe Leu Gly Leu Gln Arg Arg Gln Ala Pro Thr Gly Leu
               425                 430                 435
Gly Leu Leu Gln Ala Glu Arg Trp Glu Thr Thr Ser Cys Ala Asp
               440                 445                 450
```

Thr Gln Ser Ser His Leu His Glu Asp Arg Thr Ala Arg Val Ser
              455                 460                 465

Gln Pro Ser

<210> SEQ ID NO 3
<211> LENGTH: 258
<212> TYPE: DNA
<213> ORGANISM: Homo sapiens
<220> FEATURE: -
<223> OTHER INFORMATION: 103348H1
<220> FEATURE:
<221> NAME/KEY: unsure
<222> LOCATION: 9, 61, 68, 123, 131, 196, 214, 218, 246, 248
<223> OTHER INFORMATION: a, t, c, g, or other

<400> SEQUENCE: 3

| | | | | |
|---|---|---|---|---|
| ctacatttnc | cagatcacca | cctctctgta | ccgagctcag | cagatcatcc agctcaacat | 60 |
| ncaagctncc | cctaaagtac | gactgagctt | ggcaaacgaa | gctctgctgc ccaccctcat | 120 |
| ctncgacatt | nctggctatt | accctctgga | tgtggtggtg | acgtggaccc gagaggagct | 180 |
| gggtggattc | cccagnccaa | gtttctggtg | cctncttntc | cagcctcagg caaagcgttg | 240 |
| gcaggnanct | acagcata | | | | 258 |

<210> SEQ ID NO 4
<211> LENGTH: 533
<212> TYPE: DNA
<213> ORGANISM: Homo sapiens
<220> FEATURE: -
<223> OTHER INFORMATION: 2501017F6
<220> FEATURE:
<221> NAME/KEY: unsure
<222> LOCATION: 401, 459, 477
<223> OTHER INFORMATION: a, t, c, g, or other

<400> SEQUENCE: 4

| | | | | |
|---|---|---|---|---|
| cacacaggga | cgcgggctgc | catcttgctc | taagtgaaag | tgaaagaaaa gtcggcagca | 60 |
| gagggaacag | ggaagaaacc | taaaggctgc | aggctgccag | gtgtgcttgg agagcccct | 120 |
| tcttccgccg | ggcctcgcaa | gcagcgtagg | actgtggaga | agggcggtgg gcaaggaggg | 180 |
| aactcgagag | cagcctccat | gggcacacag | gagggctggt | gcctgctgct ctgcctggct | 240 |
| ctatctggag | cagcagaaac | caagccccac | ccagcagagg | ggcagtggcg ggcagtggac | 300 |
| gtggtcctag | actgcttcct | ggcgaaggac | ggtgcgcacc | gtggagctct cgccagcagt | 360 |
| gtaggacagg | gcaagggcct | cccttgtgct | gaagcaggtg | ncagtgctgg acgatggctc | 420 |
| cctggaggac | ttcaccgatt | tccaaggggg | cacactggnc | ccaagatgac ccaactnatt | 480 |
| aactttgagg | gctcaagtgg | acctggtcca | aaattcccca | ggccgaggct ttt | 533 |

<210> SEQ ID NO 5
<211> LENGTH: 593
<212> TYPE: DNA
<213> ORGANISM: Homo sapiens
<220> FEATURE: -
<223> OTHER INFORMATION: SASA03761F1
<220> FEATURE:
<221> NAME/KEY: unsure
<222> LOCATION: 20, 21, 24, 453, 479, 507, 521, 526, 539, 542, 549, 555,
      579, 582,
<223> OTHER INFORMATION: 589
<223> OTHER INFORMATION: a, t, c, g, or other

<400> SEQUENCE: 5

| | | | | |
|---|---|---|---|---|
| gcaggtcgac | tctagaggan | nccnctccag | ggtagcgccc | ttccgcacag cctgcccctg | 60 |

```
ccctgcggtc cagctgtaca ccaactgacc cctgcccttg tgctgcagtc gccactccac      120
actgatgagg tccaagcccg gtgccatgga aagccacag tccaaggagg ctgaggaccc       180
cagcaggaag ctcagggatt gggtctgtgt catcacctgg aactccactg cagttcgcac      240
agtcccctgg gggctcagtg gcaagttcag cgtcgggtgc cagagcgcct cattcttggt      300
gaccctggga gtcttcatca ccaaggagat gctaggtccc cctccagaga cctgcatgtt      360
ggccatgaac caagctgctg tcttaacagt ggtctctgtc atctggagaa agtagcggga      420
gatctcacag gtcaactcct ttccactgca gtnagcatgg gagcaagggc tcgggcttng      480
gggatcttgg accaaggtcc acttganggc ttcaaaagtt nattangttg ggtcaatcnt      540
tngggccant tttgncccce tttggaaaat ccggtgaant tncttccang gga             593

<210> SEQ ID NO 6
<211> LENGTH: 386
<212> TYPE: DNA
<213> ORGANISM: Homo sapiens
<220> FEATURE: -
<223> OTHER INFORMATION: SASA01221F1
<220> FEATURE:
<221> NAME/KEY: unsure
<222> LOCATION: 109, 304
<223> OTHER INFORMATION: a, t, c, g, or other

<400> SEQUENCE: 6
ccgggcaggg tgagggaggc atccctggcc atgcccagtt gtgcaggctc cagggtagcg      60
cccttccgca cagcctgccc ctgccctgcg gtccagctgt acaccaacng accctgccc      120 ttgtgctgca gtcgccactc cacactgatg aggtccaagc ccgtgccat ggagaagcca     180 cagtccaagg aggctgagga ccccagcagg aagctcaggg attgggtctg tgtcatcacc     240
tggaactcca ctgcagttcg cacagtcccc tgggggctca gtggcaagtt cagcgtcggg     300
tgcnagagcg cctcattctt ggtgaccctg ggagtcttca tcaccaagga gatgctaggt     360 cccctccag agacctgcat gttggg                                          386

<210> SEQ ID NO 7
<211> LENGTH: 616
<212> TYPE: DNA
<213> ORGANISM: Homo sapiens
<220> FEATURE: -
<223> OTHER INFORMATION: SASA01681F1
<220> FEATURE:
<221> NAME/KEY: unsure
<222> LOCATION: 440, 493, 496, 501, 535, 552, 570, 573, 576, 579, 596,
      606, 611
<223> OTHER INFORMATION: a, t, c, g, or other

<400> SEQUENCE: 7
actctagagg atcccctgt tctccgctct ggtgggacaa cctgggtgct ggccccaagg       60
ggctcctcca gagagatgtg tgtgacctgg caggtgtaag tggcacctgc agagccaggt     120
tctgcggtga gagaggagga gatgctgtag gtgcctgcca cgctttgcct gaggctggag     180
aaggaggcac cagagacttg ggctgggat ccacccagct cctctcgggt ccacgtcacc      240
accacatcca gagggtaata gccagcaatg tcgcagatga gggtgggcag cagagcttcg    300
tttgccaagc tcagtcgtac tttaggggaa gcttggatgt tgagctggat gatctgctga   360
gctcggtaca gagaggtggt gatctggcaa atgtaggtcc cctcgtcctg tatagtgagg    420
ccgggcaggg tgaaggaggn atccctggcc atgcccagtt gtgcagggct ccaaggtagc    480
ggcctttccg canagnctgc ncctggcccc tgcggttcca agcttgttac acccnaactt    540
```

```
gaaccccttg cncctttgtt gcttggccan ttngcnaant tcccaacaat tgattngaag    600
ggttcnaaaa nccccg                                                    616
```

<210> SEQ ID NO 8
<211> LENGTH: 581
<212> TYPE: DNA
<213> ORGANISM: Homo sapiens
<220> FEATURE: -
<223> OTHER INFORMATION: SASA03117F1
<220> FEATURE:
<221> NAME/KEY: unsure
<222> LOCATION: 18, 476, 500, 561, 570, 573, 575, 577, 580
<223> OTHER INFORMATION: a, t, c, g, or other

<400> SEQUENCE: 8

```
caggtcgact ctagaggntc ccccctcact atacaggacg aggggaccta catttgccag     60
atcaccacct ctctgtaccg agctcagcag atcatccagc tcaacatcca agcttcccct    120
aaagtacgac tgagcttggc aaacgaagct ctgctgccca ccctcatctg cgacattgct    180
ggctattacc ctctggatgt ggtggtgacg tggacccgag aggagctggg tggatcccca    240
gcccaagtct ctggtgcctc cttctccagc ctcaggcaaa gcgtggcagg cacctacagc    300
atctcctcct ctctcaccgc agaacccggc tctgcaggtg ccacttacac ctgccaggtc    360
acacacatct ctctggagga gccccttggg gccagcaccc aggttgtccc accagagcgg    420
agaacagcct tgggagtcat ctttgccagc agtctcttcc ttcttgcact gatgtncctg    480
gggggtttca gagacgggcn agcaacctat agggactttg gggcttgctt tcaggctgaa    540
acgcttggga gacccacttt ncctgggccn ganananaan a                        581
```

<210> SEQ ID NO 9
<211> LENGTH: 543
<212> TYPE: DNA
<213> ORGANISM: Homo sapiens
<220> FEATURE: -
<223> OTHER INFORMATION: 2842166T6
<220> FEATURE:
<221> NAME/KEY: unsure
<222> LOCATION: 109
<223> OTHER INFORMATION: a, t, c, g, or other

<400> SEQUENCE: 9

```
ccaaaggcat gtggatattt accaatgtca tgtattctga acaaaggcaa aaaatacaaa     60
ttcctaccat taaactggct tggttgttgt ttgggttgga gtagctgtng gggcttgggg    120
aagggtgtcg tttctttcta gtagtctcat gtcgctttag gtcagctggg ctggcttaca    180
cgcgctgtgc ggtcttcatg gagatgggag ctctgtgtgt cagcacagga agtggtctcc    240
cagcgttcag ccttaagcag cccaagtcct gtaggtgctg gctctttggt cttatcctcc    300
atctggacat tctgccttct tcttgtcccc tcacttcttc ctgttctctg ccttggtgca    360
tgagcccagg gtgcacagtg aaggaaggca gaggcctctg cagagccagg cccagtgccc    420
catgagctgg tgccacccttc atgtattttt aacctctgtg acttgactta aaagtccttc    480
tggggagcac gtgaactact cttgtctttc tactcttgcc gtctctgaag ccccaggaac    540
ata                                                                  543
```

<210> SEQ ID NO 10
<211> LENGTH: 247
<212> TYPE: DNA
<213> ORGANISM: Mouse
<220> FEATURE: -

<223> OTHER INFORMATION: 701322243H1
<220> FEATURE:
<221> NAME/KEY: unsure
<222> LOCATION: 191, 222, 230
<223> OTHER INFORMATION: a, t, c, g, or other

<400> SEQUENCE: 10
aagctcaaca gatcatgcca cttaacatcc tggctccccc caaagtacaa ctgcacttgg    60
caaacaagga tcctctgcct tccctcgtct gcagcattgc cggctactat cctctggatg   120
tgggagtgac gtggattcga gaggagctgg gtggaattcc agcccaagtc tctggtgcct   180
cttctccagc ntcaggcaga gcacgatggg taacttacag cnttgttcan gtgaggctga   240
cccagcc                                                             247

<210> SEQ ID NO 11
<211> LENGTH: 314
<212> TYPE: DNA
<213> ORGANISM: Rat
<220> FEATURE: -
<223> OTHER INFORMATION: 700294612H1
<220> FEATURE:
<221> NAME/KEY: unsure
<222> LOCATION: 8, 22, 70, 71, 72, 77, 78, 82, 86, 96, 130, 143, 155,
       177, 206, 216,
<223> OTHER INFORMATION: a, t, c, g, or other

<400> SEQUENCE: 11
tctctggngc ctccttctcc anccctcagac agaacatgat gggaacctac agcatttctt    60
ccacggtgan nnccganncc angccncaca ggtgcnactt acacctgcca agttgcccac   120
gtctccctgn aggagcccct ganagtcagc atgangggttt tgccaaacac agagcanaga  180
ggagccttgg gagtcatcgt tgccancatc ctcttnctttt ttgngctctt gctcctggga   240
cttcntngac agnaagcttc atcatcanag ttcnncaagt ctgtgaggna ctctgagtag    300
ncgctttnct gccc                                                     314

<210> SEQ ID NO 12
<211> LENGTH: 290
<212> TYPE: DNA
<213> ORGANISM: Rat
<220> FEATURE: -
<223> OTHER INFORMATION: 700251347H1
<220> FEATURE:
<221> NAME/KEY: unsure
<222> LOCATION: 106
<223> OTHER INFORMATION: a, t, c, g, or other

<400> SEQUENCE: 12
gttttgccaa acacagagca aagaggagcc ttgggagtca tcgttgccag catcctcttc    60 cttttttgcgc tcttgctcct gggacttcat agacagcaag cttcancatc aaagtccacc   120
aagtctgtga ggcactctga gtagccgctt tcctgcctcc gagtacaaag aaaagctctc   180
gtgttctagc tacctaagaa ccctgtgttg aggtgtggga ctgagacggg cctgaaggag   240
gcagcacatt gggagtgagg tactgaccct ggtctgtact agtctctgcc                290

<210> SEQ ID NO 13
<211> LENGTH: 212
<212> TYPE: DNA
<213> ORGANISM: Rat
<220> FEATURE: -
<223> OTHER INFORMATION: 700255439H1
<220> FEATURE:
<221> NAME/KEY: unsure
<222> LOCATION: 129

-continued

<223> OTHER INFORMATION: a, t, c, g, or other

<400> SEQUENCE: 13

| tcagttgaag ccaagcttcc cacatcctct ttgtttgcca tgaggtgatg tggggtttcc | 60 |
| attgtgtctg tcattaccac cgtgtctttc ctaacccagt ctcacagttt atgtatagta | 120 |
| gtaagagtng tccttccacc aaaggcatgt gacagattta ccaatctcat gtattctcaa | 180 |
| caaaggcgaa aaatacaaat tcctaccaca aa | 212 |

<210> SEQ ID NO 14
<211> LENGTH: 225
<212> TYPE: DNA
<213> ORGANISM: Rat
<220> FEATURE: -
<223> OTHER INFORMATION: 700124888H1

<400> SEQUENCE: 14

| catgaaggca ccaataatt tcagggaatg aggggctttg aggataacag gctctcagga | 60 |
| acacgctcca tgccatccca ctctccaatg aaagccctgt acctcccttg ttgattaaga | 120 |
| gaaatgagag ttatatggtg agactcccag ggtcccacag aacacttccc cctgcactac | 180 |
| ccacttactg tgtgtaagac aaggatgagg caggagggcc tttcc | 225 |

<210> SEQ ID NO 15
<211> LENGTH: 465
<212> TYPE: PRT
<213> ORGANISM: Homo sapiens
<220> FEATURE: -
<223> OTHER INFORMATION: g3169279

<400> SEQUENCE: 15

```
Met Lys Pro Leu Leu Leu Val Ala Val Ala Leu Gly Leu Ala
  1               5                  10                  15

Thr Phe Val Ser Val Val Ser Ala Gly Pro Glu Ala Ile Glu Cys
                 20                  25                  30

Trp Phe Val Glu Asp Ala Gly Gly Gly Leu Ser Lys Lys Pro
             35                  40                  45

Ala Thr Leu Leu Leu Arg His Gly Pro Arg Gly Pro Pro Arg
             50                  55                  60

Pro Asp Leu Asp Pro Lys Leu Tyr Phe Lys Val Asp Asp Pro Ala
             65                  70                  75

Gly Met Leu Leu Ala Ala Phe Arg Arg Tyr Pro Ala Gly Ala Ser
             80                  85                  90

Ala Pro His Cys Glu Met Ser Arg Phe Ile Pro Phe Pro Ala Ser
             95                  100                 105

Ala Lys Trp Ala Arg Ser Leu Ser Pro Glu Gln Asn Cys Pro Arg
            110                 115                 120

Ala Leu Asp Gly Asp Trp Leu Leu Val Ser Val Ser Ser Thr Leu
            125                 130                 135

Phe Ser Leu Ser Ser Leu Leu Arg Pro Gln Pro Glu Pro Leu Arg
            140                 145                 150

Glu Pro Val Val Ile Thr Met Ala Thr Val Leu Thr Val Leu
            155                 160                 165

Thr His Asn Pro Ala Pro Arg Val Gln Leu Gly Lys Asp Ala Val
            170                 175                 180

Leu Asp Leu Arg Phe Ala Tyr Ala Pro Ser Ala Leu Glu Gly Ser
            185                 190                 195
```

```
Pro Ser Leu Asp Ala Gly Pro Pro Phe Gly Leu Glu Trp Arg
            200                 205                 210

Arg Gln His Arg Gly Lys Gly His Leu Leu Ala Ala Thr Pro
            215                 220                 225

Gly Leu Ala Gly Arg Met Pro Pro Ala Gln Glu Lys Ala Thr Ala
            230                 235                 240

Phe Ala Ala Trp Asp Asp Glu Pro Trp Gly Pro Trp Thr Gly
            245                 250                 255

Asn Gly Thr Phe Trp Leu Pro Ala Val Lys Pro Ser Gln Glu Gly
            260                 265                 270

Val Tyr Leu Gly Thr Val His Leu Pro Tyr Leu Gln Gly Gln Val
            275                 280                 285

Ser Leu Glu Leu Thr Val His Lys Gly Pro Arg Val Ser Leu Thr
            290                 295                 300

Pro Ala Pro Val Val Trp Ala Ala Pro Gly Glu Ala Pro Pro Glu
            305                 310                 315

Leu Leu Cys Leu Ala Ser His Phe Phe Pro Ala Glu Gly Leu Glu
            320                 325                 330

Val Lys Trp Glu Leu Arg Gly Gly Pro Gly Gly Ser Ser Arg Lys
            335                 340                 345

Val Glu Gly Lys Thr Trp Leu Ser Thr Ile Arg His His Ser Asp
            350                 355                 360

Gly Ser Val Ser Gln Ser Gly His Leu Gln Leu Pro Pro Val Thr
            365                 370                 375

Ala Lys Gln His Gly Val His Tyr Val Cys Arg Val Tyr His Ser
            380                 385                 390

Ser Leu Pro Ala Ser Gly Arg Ser Ala Asp Val Thr Leu Glu Val
            395                 400                 405

Ala Gly Phe Ser Gly Pro Ser Ile Glu Asp Gly Ile Gly Leu Phe
            410                 415                 420

Leu Ser Ala Phe Leu Leu Leu Gly Leu Leu Lys Val Leu Gly Trp
            425                 430                 435

Leu Ala Ala Tyr Trp Thr Ile Pro Glu Val Ser Lys Glu Lys Ala
            440                 445                 450

Thr Ala Ala Ser Leu Thr Ile Pro Arg Asn Ser Lys Lys Ser Gln
            455                 460                 465

<210> SEQ ID NO 16
<211> LENGTH: 402
<212> TYPE: PRT
<213> ORGANISM: Homo sapiens
<220> FEATURE: -
<223> OTHER INFORMATION: 3183699

<400> SEQUENCE: 16

Met Ala Ala Gly Leu Arg Leu Leu Leu Ala Gly Gly Ala Arg
 1               5                  10                  15

Gly Arg Ala Ala Gly Gly Gly Gln Cys Pro Ser Cys Thr Ala Ala
            20                  25                  30

Leu Trp Gly Gly Arg Gly Asp Pro Ser Arg Thr Arg Pro Gly Ala
            35                  40                  45

Arg Ser His Leu Gln Cys Gln Arg Pro Leu Gly Asp Ser Ser Pro
            50                  55                  60

Thr Arg Val Pro Pro Arg Thr Pro Pro Ser Cys Glu Leu Asn Pro
            65                  70                  75
```

Thr Asn Pro Gln Thr Gly Ser Asp Pro Trp Ser Arg Pro Leu His
                    80                  85                  90

Pro Asp Ala Arg Ser Pro Pro Thr Ala Gly Gly Gln Trp Trp Val
                95                  100                 105

Ala Ala Val Gly Thr Pro Gln Tyr Gly Val Thr Ala Leu Leu Gln
                110                 115                 120

Gly Gly Met Gly Thr Glu Gly Thr Ile Thr Ala Ala Val Ala Leu
                125                 130                 135

Ala Val Leu Thr His Thr Pro Thr Leu Arg Ala Arg Val Gly Ser
                140                 145                 150

Pro Ile His Leu His Cys Ala Phe Ala Ala Pro Pro Ser Ser Phe
                155                 160                 165

Val Leu Glu Trp Arg His Gln Asn Arg Gly Ala Gly Arg Val Leu
                170                 175                 180

Leu Ala Tyr Asp Ser Ser Thr Ala Arg Ala Pro Arg Ala His Pro
                185                 190                 195

Gly Ala Glu Leu Leu Leu Gly Thr Arg Asp Gly Asp Gly Val Thr
                200                 205                 210

Ala Val Thr Leu Arg Leu Ala Arg Pro Ser Pro Gly Asp Glu Gly
                215                 220                 225

Thr Tyr Ile Cys Ser Val Phe Leu Pro His Gly His Thr Gln Thr
                230                 235                 240

Val Leu Gln Leu His Val Phe Glu Pro Lys Val Thr Leu Ser
                245                 250                 255

Pro Lys Asn Leu Val Val Ala Pro Gly Thr Ser Ala Glu Leu Arg
                260                 265                 270

Cys His Val Ser Gly Phe Tyr Pro Leu Asp Val Thr Val Thr Trp
                275                 280                 285

Gln Arg Arg Ala Gly Gly Ser Gly Thr Ser Gln Ser Pro Arg Asp
                290                 295                 300

Thr Val Met Asp Ser Trp Thr Ser Gly His Arg Gln Ala Ala Asp
                305                 310                 315

Gly Thr Tyr Ser Arg Thr Ala Ala Ala Arg Leu Ile Pro Ala Arg
                320                 325                 330

Pro Gln His His Gly Asp Ile Tyr Ser Cys Val Val Thr His Thr
                335                 340                 345

Ala Leu Ala Lys Pro Met Arg Val Ser Val Arg Leu Leu Ala
                350                 355                 360

Gly Thr Glu Gly Pro His Leu Glu Asp Ile Thr Gly Leu Phe Leu
                365                 370                 375

Val Ala Phe Val Leu Cys Gly Leu Ile Arg Trp Leu Tyr Pro Lys
                380                 385                 390

Ala Ala Arg Pro Lys Glu Glu Thr Lys Lys Ser Gln
                395                 400

<210> SEQ ID NO 17
<211> LENGTH: 1482
<212> TYPE: DNA
<213> ORGANISM: Rat
<220> FEATURE: -
<223> OTHER INFORMATION: g207628

<400> SEQUENCE: 17
gaattcgggt tccgtctact tcagccgcag cgtctccctg cctgtctcat tgcattctcc      60
agagagggga cggacctcca cttcctcttt cagaaaaatg tctgctccag ctcagccacc     120

```
tgctgaaggg acagaagggg ctgccccagg tgggggtcct cctggtcctc ctcccaatac      180
gaccagtaac agacgattac agcaaaccca ggcacaagtg gaggaggtgg tggacatcat      240
tcgcgtgaat gtggacaagg tcttggagag ggaccagaag ttgtcagagt tggatgaccg      300
agctgacgcc ttgcaggcag gagcgtcagt gtttgagagc agtgctgcca agctaaaaag      360
gaagtattgg tggaaaaact gcaagatgat gatcatgctg ggagctatct gtgccatcat      420
cgtggtagta attgtaatct acatttttac ttgagaatgt gccatcoctt ccctgttctc      480 cattgccatc caagctcatg tttccctct gtttgctctc tcaacaaagt cctccatctt       540
ccgttctcca tcctggccca ggcttctctg tgatccgacc ttccctttt gtgcattcat       600 tcgcactctt cctcaaaact agaaatgctg ctcgtggcac agtcctgaaa gtcactgccc      660
gaagagaaca cccagcacct cctctttacc catttatcat gtgccctgga gcttaaaaga     720
gttgtggcca atggcagagg tgaagtgtct gagaagttag catggctgag gggaagagaa     780
aggcatttgt gtccaagaaa ggctggcctt tggcaggagg gaagcaagaa tagttgggaa     840
gtagtagctt gctgccagtg tatatgtata tgtatatgta tatgtatatg tatatgtata     900
tgtatatgta tatattagtt gggaactatg acctgctgtc ctcatttgga actttcctcc     960
cataccaggc ctgtcttggg tcccagaggt ctgtttaaag accaacttca aatccctttt    1020
agaaaaacat caaacttgca ttttgtagct actgttatct gtcagtacaa gattttctgt    1080
gtctttgggg gaactttaca actttctcgt ttgtctctat agccccagga gagaagtact    1140
ttctgatttt aaaaacagca ggacactctt accttcttct agaaggcgtc ccacatgctt    1200
ctgactagaa ggagctacca cctcttcatg tcatctgaag catttgatgt tgttcatgaa    1260
ggcaccaaat aatttcaggg aatgaggggc tttgaggata acaggctctc aggaacacgc    1320
tccatgccat cccactctcc aatgaaagcc ctgtacctcc cttgttgatt aagagaaatg    1380
agagttatat ggtgagactc ccagggtccc acagaacact tccccctgca ctacccactt    1440
actgtgtgta agacaaggat gaggcaggag ggccccgaat tc                       1482
```

TAPASIN-LIKE PROTEIN

FIELD OF THE INVENTION

This invention relates to nucleic acid and amino acid sequences of a new protein and to the use of these sequences in the characterization, diagnosis, prevention, and treatment of conditions such as cancer and immune and reproductive disorders.

BACKGROUND OF THE INVENTION

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, nematode, fly, rat, and man have common chemical or structural features and modulate the same general cellular activity. Comparisons of human gene sequences with those from other organisms where the structure and/or function may be known allow researchers to draw analogies and to develop model systems for testing hypotheses. These model systems are of great importance in developing and testing diagnostic and therapeutic agents for human conditions, diseases and disorders.

Tapasin is a 48-kDa transmembrane glycoprotein. It is found in the endoplasmic reticulum (ER) and displays a cytoplasmic retention signal. Tapasin is a member of the immunoglobulin (Ig) superfamily and is encoded by an major histocompatibility (MHC)-linked gene. The protein plays a critical functional role in MHC class I-restricted antigen processing. Tapasin mediates the interaction between the transporter associated with antigen processing (TAP) and newly synthesized MHC class I molecules by forming complexes with other chaperones such as calnexin and calreticulin. Up to four MHC class I-tapasin complexes bind and present molecules to each TAP molecule. (See Pamer and Cresswell (1998) Annu. Rev. Immunol. 16:323–58; Ortmann et al. (1997) Science 277:1306–9.) Tapasin is essential for human lymphocyte (HLA) A1, B8, and B4402 antigen presentation. Although tapasin is required for HLA-A2 molecules to bind TAP, its absence affects the overall efficiency of the process of loading HLA-A2 with optimal, stabilizing peptides. With its Ig_MHC binding signature (Y)xCx(V)xB, tapasin is a necessary cofactor in a multicomponent 'peptide loading complex' where lack of binding results in proteasome-mediated degradation (Lewis et al. (1998) Eur. J. Immunol. 28:3214–20). After analysis of mutant molecules which fail to bind tapasin or TAP, Suh et al. (1999; J. Immunol. 162:1530–40) also suggest a peptide-editing function for tapasin/TAP in addition to their role in enhancing peptide loading.

Correct antigen presentation to T lymphocytes is important in the infectious disease process. In a study of the mutant MHC class I molecule T134K (in which Thr134 was changed to Lys), Lewis and Elliott (1998; Curr. Biol. 8:717–20) reported that the point mutation disrupted, directly or indirectly, the interaction between MHC class I molecules and calreticulin. T134K molecules were tranported out of the ER as 'empty' MHC class I complexes rather than being retained and degraded and neither bound TAP nor presented viral antigens to T cells.

The discovery of a nucleic acid sequence encoding a tapasin-like protein provides new compositions which are useful in the characterization, diagnosis, prevention, and treatment of conditions such as cancer and immune and reproductive disorders.

SUMMARY OF THE INVENTION

The invention is based on the discovery of a nucleic acid sequence encoding a mammalian protein, tapasin-like protein (TLP), which satisfies a need in the art by providing new compositions useful in the characterization, diagnosis, prevention, and treatment of conditions such as cancer and immune and reproductive disorders.

The invention provides an isolated and purified mammalian nucleic acid sequence comprising SEQ ID NO:1 or a fragment thereof (SEQ ID NOs:3–9). The invention further provides fragments homologous to the mammalian nucleic acid sequences from mouse and rat identified as SEQ ID NOs: 10–13 in the Sequence Listing. The invention also provides a substantially purified mammalian nucleic acid sequence encoding the amino acid sequence of SEQ ID NO:2 or a portion thereof.

The invention further provides an isolated and purified nucleic acid sequence or a fragment thereof which hybridizes under high stringency conditions to the nucleic acid sequence of SEQ ID NO:1. The invention also provides an isolated and purified nucleic acid sequence or a fragment thereof which is complementary to the nucleic acid sequence of SEQ ID NO:1. In one aspect, a single stranded complementary RNA or DNA sequence is used as a probe which hybridizes under high stringency conditions to the mammalian nucleic acid sequence or a fragment thereof.

The invention further provides a method for detecting a nucleic acid sequence in a sample, the method comprising the steps of hybridizing the complement of the nucleic acid sequence to at least one nucleic acid sequence of the sample, thereby forming a hybridization complex; and detecting the hybridization complex, wherein the presence of the hybridization complex correlates with the presence of a nucleic acid sequence in the sample. In one aspect, the method further comprises amplifying the nucleic acid sequence prior to hybridization. The nucleic acid sequence or fragment thereof may comprise either an element or a target on a microarray. The invention also provides a method for using a nucleic acid sequence or a fragment thereof to screen a library of molecules to identify at least one molecule which specifically binds the nucleic acid sequence, the method comprising providing a library of molecules, combining the nucleic acid sequence with the library of molecules under conditions suitable to allow specific binding, and detecting specific binding, thereby identifying a molecule which specifically binds the nucleic acid sequence. Such libraries include DNA and RNA molecules, peptides, PNAs, proteins, and the like which are potential regulators of replication, transcription, and translation.

The invention also provides an expression vector containing at least a fragment of the nucleic acid sequence of SEQ ID NO:1. In another aspect, the expression vector is contained within a host cell. The invention further provides a method for producing a protein, the method comprising the steps of culturing the host cell under conditions suitable for the expression of the protein and recovering the protein from the host cell culture. The invention also provides an isolated and purified protein comprising the amino acid sequence of SEQ ID NO:2 or a portion thereof. Additionally, the invention provides a pharmaceutical composition comprising a substantially purified protein having the sequence of SEQ ID NO:2 or a portion thereof in conjunction with a suitable pharmaceutical carrier.

The invention further provides a method for using a portion of the protein to produce antibodies. The invention also provides a method for using a protein or a portion thereof to screen a library of molecules to identify at least one molecule which specifically binds the protein, the method comprising providing a library of molecules, combining the protein with the library of molecules under conditions suitable to allow specific binding, and detecting specific binding, thereby identifying a molecule which specifically binds the protein. In one aspect, a molecule identified using the method modulates the activity of the protein.

The invention further provides a method for inserting a marker gene into the genomic DNA of a mammal to disrupt the expression of the natural mammalian nucleic acid sequence. The invention also provides a method for using SEQ ID NO:1 to produce a mammalian model system, the method comprises constructing a vector containing SEQ ID NO:1; introducing the vector into a suitable totipotent mammalian embryonic stem cell; selecting an embryonic stem cell with the vector integrated into genomic DNA; microinjecting the selected cell into a suitable mammalian blastocyst, thereby forming a chimeric blastocyst; transferring the chimeric blastocyst into a psuedopregnant dam, wherein the dam gives birth to a chimeric mammal containing at least one additional copy of SEQ ID NO:1 in its germ line; and breeding the chimeric mammal to generate a homozygous mammalian model system.

BRIEF DESCRIPTION OF THE FIGURES AND TABLE

FIGS. 1A, 1B, 1C, 1D, and 1E show the nucleic acid sequence (SEQ ID NO:1) encoding the amino acid sequence (SEQ ID NO:2) of the mammalian protein. The alignment was produced using MACDNASIS PRO software (Hitachi Software Engineering, South San Francisco Calif.).

FIGS. 2A, 2B, 2C, 2D, 2E, and 2F shows the alignment between SEQ ID NO:1 and SEQ ID NOs:3–13 produced using Phrap (Phil Green, University of Washington).

FIGS. 3A and 3B demonstrates the chemical and structural similarity between SEQ ID NO:2, mouse tapasin (g3169279, SEQ ID NO:15), and chicken tapasin (g3183699; SEQ ID NO:16) produced using the MEGA-LIGN program (DNASTAR, Madison WI).

Table 1 shows the Incyte clones from human, rat and mouse which have homology with SEQ ID NO:1 and includes their nucleotide length, biological source, region of overlap with SEQ ID NO:1, and percent identity with SEQ ID NO:1.

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a," "an," and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"TLP" refers to a substantially purified protein obtained from any mammalian species, including murine, bovine, ovine, porcine, rodent, canine, simian, and preferably the human species, and from any source, whether natural, synthetic, semi-synthetic, or recombinant.

"Biologically active" refers to a protein having structural, immunological, regulatory, or chemical functions of a naturally occurring, recombinant or synthetic molecule.

"Complementary" refer to the natural hydrogen bonding by base pairing between purines and pyrimidines. For example, the sequence A-C-G-T forms hydrogen bonds with its complements T-G-C-A or U-G-C-A. Two single-stranded molecules may be considered partially complementary, if only some of the nucleotides bond, or completely complementary, if nearly all of the nucleotides bond. The degree of complementarity between nucleic acid strands affects the efficiency and strength of the hybridization and amplification reactions.

"Derivative" refers to the chemical modification of a nucleic acid sequence or protein sequence. Chemical modifications of a sequence can include replacement of hydrogen by an alkyl, acyl, or amino group or glycosylation, pegylation, or any similar process which retains or enhances biological activity or lifespan of the molecule.

"Fragment" refers to an Incyte clone or any part of a nucleic acid sequence which retains a usable, functional characteristic. Useful fragments include oligonucleotides which may be used in hybridization or amplification technologies or in regulation of replication, transcription or translation.

"Hybridization complex" refers to a complex between two nucleic acid sequences by virtue of the formation of hydrogen bonds between purines and pyrimidines.

"Modulates" refers to a change in activity (biological, chemical, or immunological) or lifespan resulting from specific binding between a molecule and either a nucleic acid sequence or a protein.

The term "molecules" is used substantially interchangeably with the terms agents and compounds. Such molecules modulate the activity of nucleic acid sequences or proteins of the invention and may be composed of at least one of the following: inorganic and organic substances including nucleic acids, proteins, carbohydrates, fats, and lipids.

"Nucleic acid sequence" refers to a nucleic acid, oligonucleotide, nucleotide, polynucleotide or any fragment thereof. It may be DNA or RNA of genomic or synthetic origin, double-stranded or single-stranded, and combined with carbohydrate, lipids, protein or other materials to perform a particular activity such as transformation or form a useful composition such as a peptide nucleic acid (PNA). "Oligonucleotide" is substantially equivalent to the terms amplimer, primer, oligomer, element, target, and probe and is preferably single stranded.

"Protein" refers to an amino acid, amino acid sequence, oligopeptide, peptide, or polypeptide or portions thereof whether naturally occurring or synthetic.

"Portion", as used herein, refers to any part of a protein used for any purpose, but especially for the screening of a library of molecules which specifically bind to that portion or for the production of antibodies.

"Sample" is used in its broadest sense. A sample containing nucleic acids may comprise a bodily fluid; an extract from a cell, chromosome, organelle, or membrane isolated from a cell; genomic DNA, RNA, or cDNA in solution or bound to a substrate; a cell; a tissue; a tissue print; and the like.

Molecules or compounds which "specifically bind" the mammalian nucleic acid sequence or protein may include, nucleic acids, carbohydrates, lipids, proteins, or any other organic or inorganic molecules or their combinations which stabilize or modulate the activity of the mammalian protein.

"Substantially purified" refers to nucleic acid or amino acid sequences that are removed from their natural environment and are isolated or separated, and are at least about 60% free, preferably about 75% free, and most preferably about 90% free, from other components with which they are naturally associated.

"Substrate" refers to any suitable rigid or semi-rigid support to which nucleic acid sequences or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

THE INVENTION

The invention is based on the discovery of a new mammalian nucleic acid sequence which encodes a mammalian protein, tapasin-like protein (TLP), and the use of the nucleic acid sequence, or fragments thereof, and amino acid sequences, or portions thereof, as compositions in the characterization, diagnosis, treatment, or prevention of conditions such as cancer and immune and reproductive disorders.

Nucleic acids encoding the mammalian protein of the present invention were identified by BLAST analysis. Incyte clone number 700124888 (SEQ ID NO:14) from the rat cerebral hemisphere tissue library (RABHNOT01) which aligned with rat vesicle associated membrane protein (VAMP-1; g207628). VAMP-1 (SEQ ID NO:17) was used to identify related VAMP and tapasin-like sequences in the Incyte LIFESEQ database. These sequences SEQ ID NOs:3–9, Incyte clones (libraries) and shotgun sequences: 103348H1 (BMARNOT02),2501017F6 (ADRETUT05), SASA03761F1, SASA01221F1, SASA01681F1, SASA03117F1, and 2842166T6 (DRGLNOT01) SEQ ID NOs:3–9, respectively, contributed to the assembly of the consensus sequence, SEQ ID NO:1 (FIGS. 1A–1E).

The mammalian fragments comprising SEQ ID NO:10 from mouse and SEQ ID NO:11–13 from rat, were identified using either SEQ ID NO:10 or one of the Incyte clones, SEQ ID NOs:3–9. FIGS. 2A–2F and Table 1 show the alignment of the mammmalian sequences. Any of these sequences may be used in hybridization and amplification technologies to identify and distinguish between SEQ ID NO:1 and similar sequences in a sample. The sequences may be used to produce transgenic animal models which mimic human conditions, diseases, or disorders or to monitor animal toxicology studies, clinical trials, and subject/patient treatment profiles. Northern analysis shows expression of this sequence in various libraries, particularly hematopoietic (14%), nervous (11%) and reproductive (22%) tissues. SEQ ID NO:1 has a 53% association with inflamed, immune responsive, or infected tissues and a 47% association with cancerous or proliferating tissues.

TLP comprising the amino acid sequence of SEQ ID NO:2 is 468 amino acids in length and has a signal peptide from residue M1 to residue E20, a potential transmembrane domain from residue L408 to residue L426, nine casein kinase II phosphorylation sites at residues S53, S74, S116, T165, T187, T274, T336, S388, and S447; six protein kinase C phosphorylation sites at residues T135, T161, T184, S303, S354, and T461; and an Ig_MHC signature from residue Y380 to residue H386. FIGS. 3A and 3B demonstrate the chemical and structural similarity among TLP, mouse tapasin (SEQ ID NO:15), and chicken tapasin (SEQ ID NO:16). Of particular note are the conserved cysteine residues 39, 122, 321, 382; the shared Ig_MHC signature, Y380–H386; the conserved residues, G205, L210, E226–R228, Q230, G233, G235, D265, L270, and E278–Y281, of the Ig binding domain predicted by HMM to extend from G205–I285 and the conserved residues, L319, C321, Y327, P328, V360, W335, R337, G342, S354, and R356, of the Ig binding domain predicted by HMM to extend from L316–S358. The amino acids of SEQ ID NO:2, from residue G17 to residue V33 or from residue L110 to residue Y127 are particularly appropriate for antibody production.

Characterization and Use of the Invention
cDNA Libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. At least one library preparation representative of the invention is described in the EXAMPLES below. The consensus mammalian sequence was chemically and/or electronically assembled from fragments including Incyte clones, extension, and/or shotgun sequences using computer programs such the AUTOASSEMBLER application (Applied Biosystems (ABI), Foster City, Calif.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase, thermostable T7 DNA polymerase (Amersham Pharmacia Biotech, Piscataway N.J.), or combinations of polymerases and proofreading exonucleases such as those found in the ELONGASE amplification system (Life Technologies, Rockville Md.). Preferably, sequence preparation is automated with machines such as the HYDRA microdispenser (Robbins Scientific, Sunnyvale Calif.), MICROLAB 2200 (Hamilton, Reno NV), and the DNA ENGINE thermal cycler (PTC200; MJ Research, Watertown Mass.). Machines used for sequencing include the ABI 3700, 377 or 373 DNA sequencing systems ABI, the MEGABACE 1000 DNA sequencing system (Amersham Pharmacia Biotech), and the like. The sequences may be analyzed using a variety of algorithms which are well known in the art and described in Ausubel (1997; Short Protocols in Molecular Biology. John Wiley & Sons, New York N.Y., unit 7.7) and Meyers (1995; Molecular Biology and Biotechnology, Wiley VCH, New York N.Y., pp 856–853).

Shotgun sequencing is used to generate more sequence from cloned inserts derived from multiple sources. Shotgun sequencing methods are well known in the art and use thermostable DNA polymerases, heat-labile DNA polymerases, and primers chosen from representative of regions flanking the nucleic acid sequences of interest. Prefinished sequences (incomplete assembled sequences) are inspected for identity using various algorithms or programs well known in the art, CONSED (Gordon (1998) Genome Res. 8:195–202). Contaminating sequences including vector or chimeric sequences or deleted sequences can be removed or restored, respectively, organizing the prefinished sequences into finished sequences.

Extension of the Nucleic Acid Sequence

The sequences of the invention may be extended using various PCR-based methods known in the art. For example, the XL-PCR kit ABI, nested primers, and commercially available cDNA or genomic DNA libraries (Life Technologies; Clontech, Palo Alto Calif., respectively) may be used to extend the nucleotide sequence. For all PCR-based methods, primers may be designed using commercially available software, such as OLIGO software Molecular Biology, Insights, Cascade to be about 22 to 30 nucleotides in length, to have a GC content of about 50% or more, and to anneal to a target sequence at temperatures from about 55° C. to about 68° C. When extending a sequence to recover regulatory elements, it is preferable to use genomic, rather than cDNA libraries.

USE OF THE MAMMALIAN NUCLEIC ACID SEQUENCE

Hybridization

The nucleic acid sequence of SEQ ID NO:1 and fragments thereof can be used in various hybridization technologies for various purposes. Hybridization probes may be designed or derived from SEQ ID NO:1. Such probes may be made from a highly specific region such as the 5' regulatory region or from a conserved motif, and used in protocols to identify naturally occurring sequences encoding the mammalian protein, allelic variants, or related sequences, and should preferably have at least 50% sequence identity to any of the protein sequences. The hybridization probes of the subject invention may be DNA or RNA and may be derived from the sequence of SEQ ID NO:1 or from genomic sequences including promoters, enhancers, and introns of the mammalian gene. Hybridization or PCR probes may be produced using oligolabeling, nick translation, end-labeling, or PCR amplification in the presence of the labeled nucleotide. A vector containing the nucleic acid sequence may be used to produce an mRNA probe in vitro by addition of an appropriate RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleotide sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid sequences are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or Triton X-100 and a blocking agent such as denatured salmon sperm DNA. Selection of components and conditions for hybridization are well known to those skilled in the art and are reviewed in Ausubel (supra) and Sambrook et al. (1989) *Molecular Cloning. A Laboratory Manual*, Cold Spring Harbor Press, Plainview N.Y.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natl. Acad. Sci. 93:10614–10619; Baldeschweiler et al. (1995) PCT application W095/251116; Shalon et al. (1995) PCT application W095/35505; Heller et al (1997) Proc. Natl. Acad. Sci. 94:2150–2155; and Heller et al. (1997) U.S. Pat. No. 5,605,662.) Hybridization probes are also useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome DNA libraries.

Expression

A multitude of nucleic acid sequences capable of encoding the mammalian protein may be cloned into a vector and used to express the protein, or portions thereof, in appropriate host cells. The nucleotide sequence can be engineered by such methods as DNA shuffling (Stemmer and Crameri (1996) U.S. Pat. No. 5,830,721 incorporated by reference herein) and site-directed mutagenesis to create new restriction sites, alter glycosylation patterns, change codon preference to increase expression in a particular host, produce splice variants, extend half-life, and the like. The expression vector may contain appropriate transcriptional and translational control elements (promoters, enhancers, specific initiation signals, and 3' untranslated regions) from various sources which have been selected for their efficiency in a particular host. The vector, nucleic acid sequence, and regulatory elements are combined using in vitro recombinant DNA techniques, synthetic techniques, and/or in vivo genetic recombination techniques well known in the art and described in Sambrook (supra ch. 4, 8, 16 and 17).

A variety of host systems may be transformed with an appropriate expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. Sequences may be ligated into the non-essential E1 or E3 region of the viral genome, and the infective virus used to transform and express the protein in host cells. The Rous sarcoma virus enhancer or SV40 or EBV-based vectors may also be used for high-level protein expression Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using appropriate culture techniques. Visible markers are also used to quantify the amount of protein expressed by the introduced genes. Verification that the host cell contains the desired mammalian nucleic acid sequence is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), calmodulin binding peptide (CBP), 6-His, FLAG, MYC, and the like. GST, CBP, and 6-His are purified using commercially available affinity matrices such as immobilized glutathione, calmodulin, and metal-chelate resins, respectively. FLAG and MYC are purified using commercially available monoclonal and polyclonal antibodies. A proteolytic cleavage site may be located between the desired protein sequence and the heterologous moiety for ease of separation following purification. Methods for recombinant protein expression and purification are discussed in Ausubel (suvra unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds a-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative and the resin is washed. The full length peptide is synthesized by sequential deprotection, coupling of derivitized amino acids, and washing with dichloromethane and/or N, N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1–S20). Automated synthesis may also be carried out on machines such as the ABI 431A Peptide synthesizer ABI. A protein or portion thereof may be substantially purified by preparative high performance liquid chromatography and its composition confirmed by amino acid analysis or by sequencing (Creighton (1984) *Proteins, Structures and Molecular Properties*, W H Freeman, New York N.Y.).

Preparation and Screening of Antibodies

Various hosts including goats, rabbits, rats, mice, humans, and others may be immunized by injection with mammalian protein or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligonucleotides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol. Methods 81:31–42; Cote et al. (1983Proc. Nati. Acad. Sci. 80:2026–2030; and Cole et al. (1984) Mol. Cell Biol. 62:109–120.)

Alternatively, techniques described for the production of single chain antibodies may be adapted, using methods known in the art, to produce epitope specific single chain antibodies. Antibody fragments which contain specific binding sites for epitopes of the mammalian protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The mammalian protein may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the ar. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmnacia Biotech kits for incorporation of alabeled nucleotide such as $^{32}$P-dCTP, Cy3-dCTP or Cy5 dCTP (Amersham Phanmacia Biotech) or amino acid such as $^{35}$S-methionine American Pharmacia Biotech: Nucleic acids and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

DIAGNOSTCS

The nucleic acid sequences, fragments, oligonucleotides, complementary RNA and DNA molecules, and PNAs may be used to detect and quantify altered gene expression, absence/presence vs. excess, expression of mRNAs or to monitor mRNA levels during therapeutic intervention. Conditions, diseases or disorders associated with altered expression include acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermnatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The diagnostic assay may use hybridization or amplification technology to compare gene expression in a biological sample from a patient to standard samples in order to detect altered gene expression. Qualitative or quantitative methods for this comparison are well known in the art.

For example, the nucleotide sequence may be labeled by standard methods and added to a biological sample from a patient under conditions suitable for the formation of hybridization complexes. After a suitable incubation period, the sample is washed and the amount of label, or its signal, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a sequence or a fragment thereof under conditions suitable for hybridization or amplification. Standard hybridization may be quantified by comparing the values obtained from normal subjects with values from an experiment in which a known amount of a substantially purified nucleic acid sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) Current Protocols in Immunology, Wiley-Interscience, New York N.Y.; and Pound, supra.)

THERAPEUTICS

Chemical and structural similarity, e.g., in the context of sequences and motifs, exists between regions of the TLP and tapasins from mouse and chicken. In addition, gene expression is closely associated with hematopoietic, nervous, and reproductive tissues and appears to play a role in conditions such as cancer and immune and reproductive disorders. In the treatment of conditions associated with increased expression or activity, it is desirable to decrease expression or protein activity. In the treatment of conditions associated with decreased expression or activity, it is desirable to increase expression or protein activity.

In one embodiment, the mammalian protein or a portion or derivative thereof may be administered to a subject to treat or prevent a condition associated with altered expression or activity of the mammalian protein. Examples of such conditions include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a pharmaceutical composition comprising a substantially purified the mammalian protein in conjunction with a suitable pharmaceutical carrier may be administered to a subject to treat or prevent a condition associated with altered expression or activity of the mammalian protein including, but not limited to, those provided above.

In a further embodiment, an agonist which modulates the activity of the mammalian protein may be administered to a subject to treat or prevent a condition associated with altered expression or activity of the protein including, but not limited to, those listed above.

In an additional embodiment, a vector capable of expressing the mammalian protein or a portion or derivative thereof may be administered to a subject to treat or prevent a condition associated with altered expression or activity of protein including, but not limited to, those described above.

In yet another embodiment, an antagonist or inhibitor of the mammalian protein may be administered to a subject to treat or prevent a condition associated with altered expression or activity of the protein. In one aspect, an antibody which specifically binds the mammalian protein may be used directly as an antagonist or indirectly as a targeting or delivery mechanism for bringing a pharmaceutical agent to cells or tissue which express the mammalian protein.

In a still further embodiment, a vector expressing the complement of the nucleic acid sequence encoding the mammalian protein or fragments thereof may be administered to a subject to treat or prevent a condition associated with altered expression or activity of the protein including, but not limited to, those described above.

Any of the nucleic acids, complementary sequences, vectors, proteins, agonists, antagonists, or antibodies of the invention may be administered in combination with other appropriate therapeutic agents. Selection of the appropriate agents for use in combination therapy may be made by one of ordinary skill in the art according to conventional pharmaceutical principles. A combination of therapeutic agents may act synergistically to effect prevention or treatment of a particular condition at a lower dosage of each agent.

Modification of Gene Expression Using Nucleic Acids

Gene expression may be modified by designing complementary sequences or antisense molecules (DNA, RNA, or PNA) to the control, 5', 3' or regulatory regions of the mammalian gene. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177.) A complementary sequence may also be designed to block translation by preventing binding between ribosomes and mRNA. In one alternative, a library of nucleic acid sequences or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening Assays

The nucleic acid sequence encoding the mammalian protein may be used to screen a library of molecules for specific binding affinity. The assay can be used to screen a library of DNA molecules, RNA molecules, PNAs, peptides, or proteins including transcription factors, enhancers, repressors, and the like which regulate the activity of the nucleic acid sequence in the biological system. The assay involves providing a library of molecules, combining the mammalian nucleic acid sequence or a fragment thereof with the library of molecules under conditions suitable to allow specific binding, and detecting specific binding to identify at least one molecule which specifically binds the nucleic acid sequence.

Similarly the mammalian protein or a portion thereof may be used to screen libraries of molecules in any of a variety of screening assays. The portion of the protein employed in such screening may be free in solution, affixed to an abiotic or biotic substrate (e.g. borne on a cell surface), or located intracellularly. Specific binding between the protein and molecule may be measured. Depending on the kind of library being screened, the assay may be used to identify DNA, RNA, or PNA molecules, agonists, antagonists, antibodies, immunoglobulins, inhibitors, peptides, proteins, drugs and the like, which specifically bind the protein. One method for high throughput screening using very small assay volumes and very small amounts of test compound is described in U.S. Pat. No. 5,876,946, incorporated herein by reference, which screens large numbers of molecules for enzyme inhibition or receptor binding.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it may be expressed as the ratio, LD50/ED50. Pharmaceutical compositions which exhibit large therapeutic indexes are preferred. The data obtained from cell culture assays and animal studies are used in formulating a range of dosage for human use.

MODEL SYSTEMS

Animal models may be used as bioassays where they exhibit a toxic response similar to that of humans and where exposure conditions are relevant to human exposures. Mammals are the most common models, and most toxicity studies are performed on rodents such as rats or mice because of low cost, availability, and abundant reference toxicology. Inbred rodent strains provide a convenient model for investigation of the physiological consequences of under- or over-expression of genes of interest and for the development of methods for diagnosis and treatment of diseases. A rodent strain inbred to over-express a particular gene may also serve as a convenient source of the protein expressed by that gene.

Toxicology

Toxicology is the study of the effects of agents on living systems. The majority of toxicity studies are performed on rats or mice to help predict the effects of these agents on human health. Observation of qualitative and quantitative changes in physiology, behavior, homeostatic processes, and lethality are used to generate a toxicity profile and to assess the consequences on human health following exposure to the agent.

Genetic toxicology identifies and analyzes the ability of an agent to produce genetic mutations Genotoxic agents usually have common chemical or physical properties that facilitate interaction with nucleic acids and are most harmful when chromosomal aberrations are passed along to progeny. Toxicological studies may identify agents that increase the frequency of structural or functional abnormalities in progeny if administered to either parent before conception, to the mother during pregnancy, or to the developing organism. Mice and rats are most frequently used in these tests because of their short reproductive cycle and their capacity to be raised in numbers sufficient to satisfy statistical requirements.

Acute toxicity tests are based on a single administration of the agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Prolonged toxicity tests are based on the repeated administration of the agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents which over-express or under-express a gene of interest may be inbred and used to model human diseases or to test therapeutic or toxic agents. (See U.S. Pat. No. 4,736,866; U.S. Pat. No. 5,175,383; and U.S. Pat. No. 5,767,337; incorporated herein by reference). In some cases, the introduced gene may be activated at a specific time in a specific tissue type during fetal development or postnatally. Expression of the transgene is monitored by analysis of phenotype, tissue-specific mRNA expression, and challenged with experimental drug therapies.

Embryonic Stem Cells

Embryonic stem cells (ES) isolated from rodent embryos retain the potential to form an embryo. When ES cells are placed inside a carrier embryo, they resume normal development and contribute to all tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors for knockout strains contain a disease gene candidate modified to include a marker gene sequence which disrupts transcription and/or translation in vivo. The vector is introduced into ES cells by transformation methods such as electroporation, liposome delivery, microinjection, and the like which are well known in the art. The endogenous rodent gene is replaced by the disrupted disease gene through homologous recombination and integration during cell division. Then transformed ES cells are selected under appropriate conditions, identified, and preferably microinjected into mouse cell blastocysts such as those from the C57BL/6 mouse strain. The blastocysts are surgically transferred to pseudopregnant dams and the resulting chimeric progeny are genotyped and bred to produce heterozygous or homozygous strains.

ES cells are also used to study the differentiation of various cell types and tissues in vitro, such as neural cells, hematopoietic lineages, and cardiomyocytes (Bain et al. (1995) Dev. Biol. 168:342–357; Wiles and Keller (1991) Development 111:259–267; and Klug et al. (1996) J. Clin. Invest. 98:216–224). Recent developments demonstrate that ES cells derived from human blastocysts may also be manipulated in vitro to differentiate into eight separate cell lineages, including endoderm, mesoderm, and ectodermal cell types (Thomson (1998) Science 282:1145–1147).

Knockout Analysis

In gene knockout analysis, a region of a human disease gene candidate is enzymatically modified to include a non-mammalian gene such as the neomycin phosphotransferase gene (neo; Capecchi (1989) Science 244:1288–1292). The inserted coding sequence disrupts transcription and translation of the targeted gene and prevents biochemical synthesis of the disease candidate protein. The modified gene is transformed into cultured embryonic stem cells (described above), the transformed cells are injected into rodent blastulae, and the blastulae are implanted into pseudopregnant dams. Transgenic progeny are crossbred to obtain homozygous inbred lines.

Knockin Analysis

Totipotent ES cells, present in the early stages of embryonic development, can be used to create knockin humanized animals (pigs) or transgenic animal models (mice or rats) of human diseases. With knockin technology, a region of a human gene is injected into animal ES cells, and the human sequence integrates into the animal cell genome by recombination. Totipotent ES cells which contain the integrated human gene are handled as described above. Inbred animals are studied and treated to obtain information on the analogous human condition. These methods have been used to model several human diseases. (See, e.g., Lee et al. (1998) Proc. Natl. Acad. Sci. 95:11371–11376; Baudoin etal. (1998) Genes Dev. 12:1202–1216; and Zhuang et al. (1998) Mol. Cell Biol. 18:3340–3349).

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus monkeys (*Macaca fascicularis, Macaca mulatta*) and common marmosets (*Callithrix iacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPS are the first choice test animal. In addition, NHPS and individual humans exhibit differential sensitivities to many drugs and toxins and can be classified as "extensive metabolizers" and "poor metabolizers" of these agents.

In additional embodiments, the nucleotide sequences which encode the mammalian protein may be used in any molecular biology techniques that have yet to be developed, provided the new techniques rely on properties of nucleotide sequences that are currently known, including, but not limited to, such properties as the triplet genetic code and specific base pair interactions.

EXAMPLES

I cDNA Library and Sequence Preparation

A pooled sample of bone marrow from the breast bones of 24 males and females of Caucasian heritage whose ages ranged from 16 to 70 years was used to obtain poly $A^+$RNA (Clontech Laboratories, Palo Alto Calif.). The RNA was used to construct the cDNA library (BMARNOT02; Stratagene, La Jolla Calif.). cDNA synthesis was primed using both oligo d(T) and random hexamers, and the two cDNA preparations were processed separately. Synthetic adapter oligonucleotides were ligated onto cDNAs enabling their insertion into the UNI-ZAP vector system (Stratagene). Blue/white color selection enabled the detection of clones with cDNA inserts. The phagemid forms of individual cDNA clones were obtained by the in vivo excision process, in which the host bacterial strain was co-infected with both the library phage and an f1 helper phage. Polypeptides or enzymes derived from the library-containing phage and the helper phage nicked the DNA, initiated new DNA synthesis from defined sequences on the target DNA, and created a smaller, single stranded circular phagemid DNA molecule that included all DNA sequences of the PBLUESCRIPT phagemid and the cDNA insert. The phagemid DNA was released from the cells, purified, and used to reinfect fresh host cells (SOLR, Stratagene). Because the phagemid carried the gene for β-lactamase, newly transformed bacteria were selected on medium containing ampicillin. Then, the two cDNA preparations were combined into a single library by mixing equal numbers of bacteriophage.

The quality of the cDNA library was assessed using DNA probes, and the PBLUESCRIPT phagemid (Stratagene) was excised and infected into *E. coli* host strain XL1-BLUE (Stratagene) where double-stranded phagemid DNA was produced. cDNAs were obtained using either the QIAWELL-8 Plasmid or QIAGEN DNA purification system (QIAGEN, Chatsworth Calif.). The DNA was eluted from the purification resin and prepared for DNA sequencing and other analytical manipulations.

II Identification, Extension, Assembly, and Analyses of the Sequences

Incyte clone 700124888 (SEQ ID NO:14) from ZOOSEQ database (Incyte Genomics Palo Alto Calif.) of rat cDNA sequences was used to identify sequences in the LIFESEQ database (Incyte Genomics) related to rat vesicle associated membrane protein (VAMP-1; g207628). The first pass extended cDNAs, and shotgun sequences, SEQ ID Nos:3–9 were assembled using Phrap. The assembled sequence, SEQ ID NO:1 was translated MACDNASIS PRO software (Hitachi Software Engineering) to elucidate t he coding region, SEQ ID NO:2. The nucleotide and amino acid sequences were queried against databases such as the GenBank databases, SwissProt, BLOCKS, PRINTS, Prosite, and PFAM using BLAST. Motifs (source) and HMM algorithms were used to perform functional analyses, and the antigenic index (Jameson-Wolf analysis) was determined using LASERGENE software (DNASTAR). Then, the clones and assembled sequence were compared using BLAST across all mammalian libraries to identify homologous nucleic acid sequences, SEQ ID NOs: 10–13.

III Sequence Similarity

Sequence similarity was calculated as percent identity based on comparisons between at least two nucleic acid or amino acid sequences using the clustal method of the MEGALIGN program (DNASTAR). The clustal method uses an algorithm which groups sequences into clusters by examining the distances between all pairs. After the clusters are aligned pairwise, they are realigned in groups. Percent similarity between two sequences, sequence A and sequence B, is calculated by dividing the length of sequence A, minus the number of gap residues in sequence A, minus the number of gap residues in sequence B, into the sum of the residue matches between sequence A and sequence B, times one hundred. Gaps of very low or zero similarity between the two sequences are not included.

IV Northern Analysis

Northern analysis is a laboratory technique used to detect the presence of a transcript of a gene and involves the hybridization of a labeled nucleotide sequence to a membrane on which RNAs from a particular cell type or tissue have been bound.

Analogous computer techniques applying BLAST were used to search for identical or related molecules in nucleotide databases such as GenBank or LIFESEQ (Incyte Genomics). Sequence-based analysis is much faster than membrane-based hybridization, and the sensitivity of the computer search can be modified to determine whether any particular match is categorized as exact or similar. The basis of the search is the product score which is defined as: (percent sequence identity x percent maximum BLAST score) divided by 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

The results of northern analyses are reported as a percentage distribution of libraries in which the transcript encoding the mammalian protein occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease categories included cancer, inflammation/trauma, cell proliferation, and neurological. For each category, the number of libraries expressing the sequence was counted and divided by the total number of libraries across all categories.

V Extension of Nucleic Acid Sequences

The nucleic acid sequence of SEQ ID NO:1 was produced by extension of at least one Incyte cDNA clone using oligonucleotide primers. One primer was synthesized to initiate 5' extension of the known fragment, and the other, to initiate 3' extension of the known fragment. The initial primers were designed using OLIGO software Molecular Biology Insights to be about 22 to 30 nucleotides in length, to have a GC content of about 50%, and to anneal to the target sequence at temperatures of about 55° C. to about 68° C. Any fragment which would result in hairpin structures and primer-primer dimerizations was avoided. Selected human cDNA libraries were used to extend the sequence. If more than one extension was necessary or desired, additional or nested sets of primers were designed.

High fidelity amplification was obtained by performing PCR in 96-well plates using the PTC-200 (MJ Research). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair selected from the plasmid: Step 1: 94° C., 3 min; Step 2: 94° C., 15 sec; Step 3: 60° C., I min; Step 4: 68° C., 2 min; Step 5: Steps 2, 3, and 4 repeated 20 time; Step 6: 68° C., 5 min; Step 7: storage at 4° C. In the alternative, parameters for the primer pair, T7 and SK+(Stratagene), were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v); Molecular Probes, EugeneOR) dissolved in 1×TE and 0.5 μl of undiluted PCR product into each well of an opaque fluorimeter plate (Corning Costar, Acton Mass. and allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successful in producing longer sequence.

The extended sequences were desalted, concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested fragments were separated on about 0.6–0.8% agarose gels, fragments were excised as visulaized under UV light, and agar removed/digested with AGAR-ACE (Promega). Extended fragments were religated using T4 DNA ligase (New England Biolabs, Beverly Mass. into pUC 18 vector (Amersham Pharmacia Biotech), treated with Pfu DNA polymerase (Stratagene) to fill-in restriction site overhangs, and transformed into competent E. coli cells. Transformed cells were selected on antibiotic-containing media, and individual colonies were picked and cultured overnight at 37° C in 384-well plates in LB/2×carbenicillin liquid media.

The cells were lysed, and DNA was amplified using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the conditions described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit ABI.

In like manner, the nucleotide sequence of SEQ ID NO:1 is used to obtain regulatory sequences using the procedure above, oligonucleotides designed for outward extension, and an appropriate genomic DNA library.

VI Labeling of Probes and Hybridization Analyses
Blotting

Nucleic acid sequences are isolated from a biological source and applied to a solid matrix (a blot) suitable for standard nucleic acid hybridization protocols by one of the following methods. A mixture of target nucleic acids, a restriction digest of genomic DNA, is fractionated by electrophoresis through an 0.7% agarose gel in 1×TAE [Tris-acetate-ethylenediarnine tetraacetic acid (EDTA)] running buffer and transferred to a nylon membrane by capillary transfer using 20×saline sodium citrate (SSC). Alternatively, the target nucleic acids are individually ligated to a vector and inserted into bacterial host cells to form a library. Target nucleic acids are arranged on a blot by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALiNKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 beads (Amersham Pharmacia Biotech). Purified target nucleic acids are robotically arrayed onto a glass microscope slide (Corning Science Products, Corning N.Y.). The slide is previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

Probe Preparation cDNA probe sequences are made from mRNA templates. Five micrograms of mRNA is mixed with 1 µg random primer (Life Technologies), incubated at 70° C. for 10 minutes, and lyophilized. The lyophilized sample is resuspended in 50 µl of 1× first strand buffer (cDNA Synthesis systems; Life Technologies) containing a DNTP mix, [α-$^{32}$P]dCTP, dithiothreitol, and MMLV reverse transcriptase (Stratagene), and incubated at 42° C. for 1–2 hours. After incubation, the probe is diluted with 42 µl dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 Micro-Column (Amersham Pharmacia Biotech). Probes can be labeled with fluorescent markers, Cy3-dCTP or Cy5-dCTP (Amersham Pharmacia Biotech), in place of the radionuclide, [$^{32}$P]dCTP.

Hybridization

Hybridization is carried out at 65° C. in a hybridization buffer containing 0.5 M sodium phosphate (pH 7.2), 7% SDS, and 1 mM EDTA. After the blot is incubated in hybridization buffer at 65° C. for at least 2 hours, the buffer is replaced with 10 ml of fresh buffer containing the probe sequences. After incubation at 65° C. for 18 hours, the hybridization buffer is removed, and the blot is washed sequentially under increasingly stringent conditions, up to 40 mM sodium phosphate, 1% SDS, 1 mM EDTA at 65° C. To detect signal produced by a radiolabeled probe hybridized on a membrane, the blot is exposed to a PHOSPHORIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the blot is examined by confocal laser microscopy, and images are collected and analyzed using GEMTOOLS gene expression analysis software (Incyte Genomics).

VII Complementary Nucleic Acid Sequences

Sequences complementary to the nucleic acid sequence, or a fragment thereof, are used to detect, decrease, or inhibit gene expression. Although use of oligonucleotides comprising from about 15 to about 30 base pairs is described, essentially the same procedure is used with larger or smaller fragments or their derivatives (PNAs). Appropriate oligonucleotides are designed using OLIGO software Molecular Biology Insights and SEQ ID NO:1 or its fragments, SEQ ID NOs:3–9. To inhibit transcription by preventing promoter binding, a complementary oligonucleotide is designed to bind to the most unique 5' sequence, most preferably about 10 nucleotides before the initiation codon of the open reading frame. To inhibit translation, a complementary oligonucleotide is designed to prevent ribosomal binding to the mRNA encoding the mammalian protein.

VIII Expression of the Mammalian Protein

Expression and purification of the mammalian protein are achieved using bacterial or virus-based expression systems.

For expression in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express the mammalian protein upon induction with isopropyl beta-D-thiogalactopyranoside (IPTG). Expression in eukaryotic cells is achieved by infecting *Spodoptera frugimerda* (Sf9) insect cells with recombinant baculovirus, *Autographica californica* nuclear polyhedrosis virus. The nonessential polyhedrin gene of baculovirus is replaced with the mammalian cDNA by either homologous recombination or bacterial-mediated transposition involving transfer plasmid intermediates. Viral infectivity is maintained and the strong polyhedrin promoter drives high levels of cDNA transcription.

In most expression systems, the mammalian protein is synthesized as a fusion protein with, e.g., glutathione S-transferase (GST) or a peptide epitope tag, such as FLAG, permitting rapid, single-step, affinity-based purification of recombinant fusion protein from crude cell lysates. GST enables the purification of fusion proteins on immobilized glutathione under conditions that maintain protein activity and antigenicity (Amersham Pharmacia Biotech). Following purification, the GST moiety can be proteolytically cleaved from the mammalian protein at specifically engineered sites. FLAG, an 8-amino acid peptide, enables immunoaffmity purification using commercially available monoclonal and polyclonal anti-FLAG antibodies (Eastmnan Kodak). 6-His, a stretch of six consecutive histidine residues, enables purification on metal-chelate resins (QIAGEN). Methods for protein expression and purification are discussed in Ausubel (suora unit 16). Purified mammalian protein obtained by these methods can be used directly in the following activity assay.

IX Functional Assays

Protein function is assessed by expressing the sequences encoding TLP at physiologically elevated levels in mammalian cell culture. The nucleic acid sequence is subcloned into PCMV SPORT vector (Life Technologies), which contains the strong cytomegalovirus promoter, and 5–10 µg of the vector is transformed into a endothelial or hematopoietic human cell line using transformation methods well known in the art. An additional 1–2 µg of a plasmid containing sequence encoding CD64-GFP (Clontech) is co-transforrned to provide an fluorescent marker to identify transformed cells using flow cytometry (FCM).

The influence of the introduced genes on expression can be assessed using purified populations of these transformed cells. Since CD64-GFP, which is expressed on the surface of transformed cells, binds to conserved regions of human immunoglobulin G (IgG), the transformed cells is separated using magnetic beads coated with either human IgG or antibody against CD64 (DYNAL, Lake Success N.Y.). mRNA is purified from the cells and analyzed by hybridization techniques.

X Production of TLP Specific Antibodies

TLP substantially purified using polyacrylamide gel electrophoresis is used to immunize rabbits and to produce antibodies using standard protocols.

Alternatively, the amino acid sequence of TLP is analyzed using LASERGENE software (DNASTAR) to determine regions of high immunogenicity. An immunogenic epitope such as those near the C-terminus or in hydrophilic regions is selected, synthesized, and used to raise antibodies by means known to those of skill in the art.

Typically, epitopes of about 15 residues in length are produced using an ABI 431 A Peptide synthesizer ABI using Fmoc-chemistry and coupled to KLH (Sigma-Aldrich) by reaction with N-maleimidobenzoyl-N-hydroxysuccinimide ester to increase immunogenicity. Rabbits are immunized with the epitope-KLH complex in complete Freund's adjuvant. Immunizations are repeated at intervals thereafter in incomplete Freund's adjuvant. After a sufficient period of time, antisera are drawn and tested for antipeptide activity. Testing involves binding the peptide to plastic, blocking with 1% bovine serum albumin, reacting with rabbit antisera, washing, and reacting with radio-iodinated goat anti-rabbit Igu. Methods well known in the art are used to determine antibody titer and the amount of complex formation.

XI Purification of Naturally Occurring Protein Using Specific Antibodies

Naturally occurring or recombinant mammalian protein is substantially purified by immunoaffinity chromatography using antibodies specific for the protein. An immunoaffinity column is constructed by covalently coupling the antibody to CNBr-activated SEPHAROSE resin (Amersharn Pharmacia Biotech). Media containing the protein is passed over the immunoaffinity column, and the column is washed using high ionic strength buffers in the presence of detergent to allow preferential absorbance of the protein. After coupling, the column is eluted using a buffer of pH 2–3 or a high concentration of urea or thiocyanate ion to disrupt antibody/protein binding, and the protein is collected.

XII Screening Molecules for Specific Binding with the Nucleic Acid Sequence or Protein The nucleic acid sequence, or fragments thereof, or the protein, or portions thereof, are labeled with $^{32}$P-dCTP, Cy3-dCTP, Cy5-dCTP (Amershain Pharmaca Biotech), or BIODIPY or FITC (Molecular Probes,), respectively. Libraries of candidate molecules previously arranged on a suitable substrate are incubated in the presence of labeled nucleic acid sequence or protein. After incubation for a suitable period under appropriate conditions for the nucleic acid sequence or protein, the substrate is washed, and any position on the substrate retaining label, which indicates specific binding or complex formation, is assayed, and the binding molecule is identified. Data obtained using different concentrations of the nucleic acid or protein are used to calculate affinity between the labeled nucleic acid or protein and the bound molecule.

XIII Demonstration of Protein Activity

TLP activity may be demonstrated by the binding of TLP to TAP using an in vitro assay (Ravichandran (1996) J. Biol. Chem. 271:13300–03). TLP is radiolabeled with $^{35}$S, and a TAP binding substrate is prepared in the form of a glutathione S-transferase (GST)TAP fusion protein. For each assay, approximately 2 mg of GST-TAP fusion protein absorbed to glutathione-agarose beads is incubated with varying amounts of $^{35}$S-labeled TLP in a suitable buffer for 3 hours at 4° C. The agarose beads are separated from the incubation by sedimentation and washed several times to remove unbound protein. TLP and other bound proteins are solubilized from the agarose beads by boiling in wash buffer and separated by SDS-polyacrylamide gel electrophoresis. Bound TLP is visualized by autoradiography, and the amount of radioactivity is proportional to the binding of activity of TLP in the assay.

TABLE 1

| SEQ ID NO | CLONE NUMBER | NUCLEOTIDES | SOURCE | LIBRARY | ALIGNMENT | % IDENTITY |
|---|---|---|---|---|---|---|
| 1 | 103348CB1 | 1764 | Human | BMARNOT02 | 1–1764 | |
| 3 | 103348H1 | | Human | | 1038–1276 | |
| 4 | 2501017F6 | | Human | ADRETUT05 | 1–535 | |
| 5 | SASA03761F1 | | Human | | 404–1001 | |
| 6 | SASA01221F1 | | Human | | 636–1025 | |
| 7 | SASA01681F1 | | Human | | 830–1450 | |
| 8 | SASA03117F1 | | Human | | 1003–1588 | |
| 9 | 2842166T6 | | Human | DRGLNOT01 | 1237–1797 | |
| 10 | 701322243H1 | 247 | Mus musculus | MOAPUNT01 | 1082–1331 | 81 |
| 11 | 700294612H1 | 314 | Rattus norvegicus | RABFNOT02 | 1403–1490 | 75 |
| 12 | 700251347H1 | 290 | Rattus norvegicus | RABMNOT01 | 1403–1497 | 80 |
| 13 | 700255439H1 | 212 | Rattus norvegicus | RABMNOT02 | 1764–1694 | 90 |

What is claimed is:

1. A purified polynucleotide consisting of a nucleic acid sequence encoding the amino acid sequence of SEQ ID NO:2.

2. A purified polynucleotide consisting of a nucleic acid sequence of SEQ ID NO:1.

3. A composition comprising the polynucleotide of claim 1 and a label.

4. An expression vector comprising the polynucleotide of claim 1.

5. A host cell containing the expression vector of claim 4.

6. A method for using a polynucleotide to produce a protein, the method comprising the steps of:
(a) culturing the host cell of claim 8 under conditions for the expression of the protein; and
(b) recovering the protein from the host cell culture.

7. A method for detecting a polynucleotide in a sample containing nucleic acids, the method comprising the steps of:
(a) hybridizing the polynucleotide of claim 1 to at least one nucleic acid in the sample, thereby forming a hybridization complex; and
(b) detecting the hybridization complex, wherein the presence of the hybridization complex correlates with the presence of the polynucleotide in the sample.

8. The method of claim 7 further comprising amplifying the nucleic acids of the sample prior to hybridization.

* * * * *